United States Patent
Durst et al.

(10) Patent No.: US 6,248,596 B1
(45) Date of Patent: Jun. 19, 2001

(54) LIPOSOME-ENHANCED IMMUNOASSAY AND TEST DEVICE

(75) Inventors: Richard Allen Durst, Romulus; Stuart Graham Reeves; Sui Ti Atienza Siebert, both of Geneva, all of NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/034,086

(22) Filed: Mar. 3, 1998

Related U.S. Application Data

(62) Division of application No. 08/135,741, filed on Oct. 12, 1993, now Pat. No. 5,789,154.

(51) Int. Cl.$^7$ .................. G01N 33/543; G01N 33/558
(52) U.S. Cl. .............. 436/518; 422/50; 422/55; 422/56; 422/57; 422/58; 422/61; 422/82.01; 435/287.1; 435/287.2; 435/287.7; 435/287.9; 435/288.7; 435/805; 435/810; 435/970; 436/164; 436/169; 436/172; 436/514; 436/528; 436/530; 436/533; 436/805; 436/806; 436/810; 436/829; 204/403
(58) Field of Search .................. 422/50, 55–58, 422/61, 82.01; 435/287.1, 287.2, 287.7, 287.9, 288.7, 805, 810, 970; 436/164, 169, 172, 514, 518, 528, 530, 533, 805, 806, 810, 829; 204/400, 403

(56) References Cited

U.S. PATENT DOCUMENTS

| | | |
|---|---|---|
| 4,048,298 | 9/1977 | Niswender . |
| 4,235,601 | 11/1980 | Deutsch et al. . |
| 4,517,288 | 5/1985 | Giegel et al. . |
| 4,517,303 | 5/1985 | Freytag et al. . |
| 4,594,327 | 6/1986 | Zuk . |
| 4,636,479 | 1/1987 | Martin et al. . |
| 4,668,619 | 5/1987 | Greenquist et al. . |
| 4,703,017 | 10/1987 | Campbell et al. . |
| 4,752,572 | 6/1988 | Sundberg et al. . |

(List continued on next page.)

FOREIGN PATENT DOCUMENTS

| | | |
|---|---|---|
| 2-204398 | 11/1988 | (GB) . |
| WO 94/03809 | 2/1994 | (WO) . |

OTHER PUBLICATIONS

Reeves et al., "Novel Optical Measurement Approach for the Quantitation of Liposome Immunomigration Assays," *Analytical Letters*, 28:2347–2352 (1995).

(List continued on next page.)

*Primary Examiner*—Christopher L. Chin
(74) *Attorney, Agent, or Firm*—Nixon Peabody LLP

(57) ABSTRACT

A test device for detecting or determining an analyte in a test solution includes an absorbent material having separate contact, competitive binding, and measurement portions. The contact portion is positioned for contact with and uptake of the test solution. The competitive binding portion has a binding material for the analyte non-diffusively bound thereto. The measurement portion has a receptor for the analyte and marker-encapsulating liposomes non-diffusively bound thereto. In a method for using the test device, a solution containing the analyte and the analyte-liposome conjugate is allowed to traverse the absorbent material from the contact portion through the competitive binding portion and on through the measurement portion of the absorbent material. The amount of marker in the measurement portion of the absorbent material, following traversal by the test solution, is then determined as a measure of the analyte in the sample. Liposomes encapsulating an electroactive marker are used in conjunction with a test device as described above but which includes an electrochemical measurement portion in place of the measurement portion described above. Test devices and methods employing electrochemical detection or quantification of an electroactive marker corresponding to the amount of analyte in a sample may be either amperometric or potentiometric.

6 Claims, 7 Drawing Sheets

U.S. PATENT DOCUMENTS

| | | |
|---|---|---|
| 4,806,311 | 2/1989 | Greenquist . |
| 4,874,710 | 10/1989 | Piran . |
| 4,916,080 | 4/1990 | Imai et al. . |
| 4,920,046 | 4/1990 | McFarland et al. . |
| 4,939,098 | 7/1990 | Suzuki et al. . |
| 5,006,473 | 4/1991 | Bouma et al. . |
| 5,081,013 | 1/1992 | Rovelli et al. . |
| 5,085,987 | 2/1992 | Olson . |
| 5,096,629 | 3/1992 | Nanba et al. . |
| 5,141,751 | 8/1992 | Tomikawa et al. . |
| 5,198,367 | 3/1993 | Aizawa et al. . |
| 5,308,775 | 5/1994 | Donovan et al. . |
| 5,310,650 | 5/1994 | McMahon et al. . |
| 5,346,832 | 9/1994 | Aizawa et al. . |
| 5,354,692 | 10/1994 | Yang et al. . |
| 5,384,264 | 1/1995 | Chen et al. . |

OTHER PUBLICATIONS

Roberts et al., "Investigation of Liposome–Based Immunomigration Sensors for the Detection of Polychlorinated Biphenyls," *Analytical Chemistry*, 67:482–491 (1995).

Siebert et al., "Liposome Immunomigration Field Assay Device for Alachlor Determination," *Analytica Chimica Acta*, 282:297–305 (1993).

Durst, "Automated Analyzer for the Determination of Potassium and Sodium in Whole Blood," *Clinica Chimica Acta*, 80:225–234 (1977).

Durst et al., "Organic Electrochemical Techniques Having Potential Clinical Application," *Clinical Chemistry*, 28:1922–1930 (1982).

Zuk, et al., Enzyme Immunochromatography–A Quantitative Immunoassay Requiring no Instrumentation, *Clin. Chem.*, 31:7, 1144–50 (1985).

Heath–Fracica, et al., Evaluation of a New Latex Agglutination Test for Detection of Streptococcal Antibodies, *Diagn. Microbiol. Infect. Dis.*, vol. 8, pp. 25–30 (1987).

Murray et al., "Chemically Modified Electrodes Molecular Design for Electroanalysis," *Analytical Chemistry*, 59:379A–390A (1987).

Kannuck et al., "Measurement of Liposome–Released Ferrocyanide by a Dual–Function Polymer Modified Electrode," *Anal. Chemistry*, 60:142–147 (1988).

Durst, et al., Chemically Modified Electrode for Liposome-–Mediated Homogeneous Imunoassay, 5th Symposium on Ion–Selective Electrodes, *Pergamon Press*, Oxford (1989).

Monroe, Novel Liposome Immunoassays for Detecting Antigens, Antibodies and Haptens, *J. Liposome Res.*, vol. 1, pp. 339–377 (1989–90).

Plant, et al., Generic Liposome Reagent for Immunoassays, *Anal. Biochem.*, vol. 176, pp. 420–426 (1989).

Allen, et al., A Noninstrumented Quantitive Test System and Its Application for Determining Cholestrol Concentration in Whole Blood, *Clin. Chem.*, vol. 36, pp. 1591–1597 (1990).

Durst, et al., Automated Liposome–Based Flow Injection Immunoassay System, GBF (Gesellschaft für Biotechnologische Forschung) Monographs, vol. 14, pp. 181–190 (1990).

Locascio–Brown, et al., Liposome Flow Injection Immunoassay: Implications for Sensitivity, Dynamic Range, and Antibody Regeneration, *Analytical Chemistry*, pp. 2587–2593 (Dec. 1, 1990).

Collard–Bovy, C., et al., Microparticle–Enhanced Nephelometric Immunoassay. I. Measurement of $\alpha_s$–Casein and $\alpha$–Casein, *J. Dairy Sci.*, vol. 74, pp. 3695–3701 (1991).

Yap, et al., Liposome Flow Injection Immunoassay: Model Calculations of Competitive Immunoreactions Involving Univalent and Multivalent Ligands, *Analytical Chemistry*, 63:2007–11 (Sep. 15, 1991).

Armbruster, et al., Screening for Drugs of Abuse with the Roche ONTRAK Assays, *J. Anal. Tox.*, vol. 16, pp. 172–175 (May/Jun. 1992).

Durst et al., "Development of Liposome–Enhanced Immuno–Biosensing Devices for Field Measurements of Toxic Substrances," *2nd Bioelectroanalytical Symposium*, Mátrafüred, 1992, Akadémiai Kiadó, Budapest.

Pinnaduwage, et al., Stable Target–Sensitive Immunoliposomes, *Biochemistry*, vol. 31, pp. 2850–2855 (1992).

Babbitt, et al., Contact–Dependent, Immunecomplex–Mediated Lysis of Hapten–Sensitized Liposomes, *Bioconjugate Chem.*, vol. 4, pp. 199–205 (1993).

Durst et al., "Immunosensor for Extra–Lab Measurements Based on Liposome Amplification and Capillary Migration," *Biosensors & Bioelectronics*, 8:xii–xv (1993)–.

Losso, et al., Development of a Particle Concentration Fluorescence Immunoassay for the Quantitative Determination of IgG in Bovine Milk, *J. Agric. Food Chem.*, vol. 41, pp. 682–686 (1993).

Lou, et al., One–Step Competitive Immunochromatographic Assay for Semiquantitative Determination of Lipoprotein(a) in Plasma, *Clin. Chem.*, vol. 39, pp. 619–624 (1993).

Parsons et al., "Multianalyte Assay System Developed for Drugs of Abuse," *Clin. Chem.*, 39:1899–1903 (1993).

Rosenzweig, et al., Laser–Based Particle–Counting Microimmunoassay for the Analysis of Single Human Erythrocytes, *Anal. Chem.*, vol. 66, pp. 1771–1776 (1994).

US 6,248,596 B1

LIPOSOME-ENHANCED IMMUNOASSAY AND TEST DEVICE

This is a division of U.S. patent application Ser. No. 08/135,741, filed on Oct. 12, 1993, now U.S. Pat. No. 5,789,154.

This invention was made with the support of the National Institutes of Health, Grant No. 1-P42-ES-05950-01. The Government may have certain rights in the invention.

FIELD OF THE INVENTION

The present invention relates to a method for detecting or determining one or more analytes, and a test device used in the method. More particularly, the invention relates to a single-use test strip for use in an immunomigration assay employing marker-loaded liposomes for signal amplification.

BACKGROUND OF THE INVENTION

There is an increasing need for rapid, reliable, and inexpensive methods for detecting and measuring pollutants and contaminants in the environment and in food sources. Conventional analytical methods such as high pressure liquid chromatography, gas chromatography/mass spectroscopy, atomic absorption spectroscopy, etc. are particularly unsuitable for use in the field, because such methods are generally complex and employ instruments and equipment which are expensive and susceptible to damage from transport and possible contamination in the field. Gathering samples in the field for analysis at a remote laboratory is similarly unsatisfactory, because it may take a few days to several weeks from sample acquisition to obtain the results.

The need for simple, rapid, and inexpensive field assays has led to an investigation of immunoassays for surveying environmental contamination. Immunoassays comprise one category of specific binding assays, which generally rely on the affinity of naturally occurring receptors or antibodies for specific compounds. The specific binding pairs employed in immunoassays are either an antigen or a hapten, and the antibody produced in immune response to the antigen or hapten.

Competitive immunoassays are generally based upon the competition between a specific analyte, the amount of which is to be determined, and a labelled form of the analyte or an appropriate analog thereof, which is used as an indicator, for a limited number of available binding sites on a binding material specific for the analyte. Using a known amount of the labelled analyte, the amount of analyte in the sample can be determined by measuring the amount of the unbound labelled analyte, which in some systems is physically separated from the bound indicator during the assay. Alternatively, where it is possible to distinguish bound from unbound indicator, such as where detectable physical or chemical changes in the indicator occur as a result of the binding reaction, an assay can be completed without separating the bound and unbound indicator.

The types of materials commonly used as immunoassay label materials or markers include various enzymes, fluorescent dyes, chemiluminescent reactants, and radioisotopes. Such materials are often conjugated to the analyte, as in the case of enzymes and radioisotopes, or less frequently, carried within sacs such as animal erythrocytes, polymer microcapsules, or liposomes.

Immunoassays have been widely used for medical diagnosis for many years. More recently, immunoassays have been more broadly applied for the determination of toxic substances in the environment and in food. Practical applications for immunoassays in environmental analysis include evaluating the geographical scope and magnitude of pollutants, monitoring the fate and persistence of contaminants, and assessing the effectiveness of remediation efforts. Raw and processed foods must similarly be tested for chemical and biological contamination.

A wide variety of immunoassays, reagents, and test devices which exploit the interaction between the members of specific binding pairs to detect or measure a substance in a test sample have been developed.

Sophisticated, automated immunoassay systems are successfully employed in laboratory settings, but there are also many types of portable sensing devices which can be used outside the laboratory. Some portable immunoassays and test devices have even been developed for use in the home by untrained personnel. Home pregnancy test kits are an example of such immunoassay test kits.

An immunochromatographic assay method for whole blood samples is described in U.S. Pat. No. 4,594,327 to Zuk. At least one member of the specific binding pair is uniformly bound to the entire surface of a solid bibulous element. The element is contacted with the whole blood sample containing the analyte in an aqueous medium so that the sample traverses the element to define a border related to the amount of analyte. The analyte concentration is directly related to the distance the analyte has traversed. Zuk further describes determination of the border by a separate development step, such as an enzyme or chromophore signal production and amplification system.

U.S. Pat. No. 5,085,987 to Olson also describes an immunoassay employing a bibulous element such as a piece of paper affixed to plastic with adhesive. The element is contacted with the test solution suspected of containing the analyte, to which has been added an antibody for the analyte and a conjugate of the analyte and a label. The element contains a first receptor for the conjugate which is bound to a situs on the element separated from the contact portion, and a second receptor capable of binding the antibody for the analyte, which is bound to the element between the first receptor and the contact portion. The test solution moves along the element by capillary action. The situs is examined for the presence of conjugate, either by exposing the situs to a signal producing means capable of interacting with the label to produce a signal in a separate development step, such as an enzyme-catalyst-substrate system, or by directly measuring the signal from a radioactive label.

U.S. Pat. No. 4,939,098 to Suzuki, et al. discloses an immunoassay device for simultaneous determination of at least two components in a sample. At least two reagents, each of which reacts specifically with one of the components in the sample, are supported in optional places on a development layer. Residual components in the sample which do not react with the reagent first contacted by the sample continue to be moved past the place on the development layer where the first reagent is supported. After the movement of the unreacted components past each of the reagent places, the amount of the two reaction products still held in the development layer are measured. Test reagents may be included in liposomes, which are immobilized on the development layer by physical adsorption or chemical bonding.

In Suzuki, a detectable label substance such as a chelating agent, an enzyme or a fluorescent substance may be enclosed in the liposomes in addition to the antibody or antigen test reagents for qualitative or quantitative analysis of sample components. The liposomes or other label sacs are lysed by the antigen-antibody reaction or complementary activity, to release label for detection or quantification. Suzuki further describes an electric measurement method in which the liposomes contain a substance detectable with electrodes. A solution of the liposomes is removed from the development layer, and the amount of the component to be measured is quantified from the amount of signal in the electrode.

As a result of the complexity of the device and method described in Suzuki, Suzuki's technique is not well-suited for use in the field, or for use by untrained personnel. High voltage is required for the electrophoretic separation method, for example.

Immunoassays employing liposomes for signal production are described in U.S. Pat. Nos. 4,874,710 to Piran and 4,703,017 to Campbell. In Piran, the sample containing the analyte is contacted with a binder for the analyte in the presence of a conjugate of a ligand coupled to a sac lysing agent. The ligand may be designed to bind either with the analyte or the binder. Unbound conjugate, which includes a sac lysing agent, comes into contact with immobilized liposomes, which release a detectable marker. Signal from the marker is measured in the aqueous assay medium. The binder and sacs may be placed on different portions of a solid support, such as a "dip stick" which may be inserted into and withdrawn from the assay medium.

Campbell discloses an immunoassay for determination of an analyte using a tracer, such as the analyte labelled with liposome-encapsulated markers. The tracer can be visually determined without instrumentation and without further treatment of the tracer (such as sac lysing). A binder for at least one of the analyte and the tracer is supported on a test area of a solid support, which is preferably nitrocellulose in the form of a card, test strip, or dipstick. Detection or quantification of the signal, e.g., color from a dye, is made in the test area of the device. Competitive, sandwich, and inhibition embodiments of the assay are disclosed.

In view of the above-noted deficiencies and complexities of prior techniques for use as rapid, reliable, and simple field assays, the need remains for technology which will accurately detect and determine analytes such as environmental and food contaminants.

SUMMARY OF THE INVENTION

The present invention relates to a test device for detecting or determining an analyte in a test solution. The test device includes an absorbent material, having a contact portion proximate to one end for contact with and uptake of the test solution. Positioned away from the first end of the absorbent material, there is a measurement portion to which is non-diffusively bound a receptor for a conjugate of the analyte to be determined and liposomes which encapsulate a detectable marker. The test device further includes a competitive binding portion positioned between and segregated from the contact and measurement portions. A binding material for the analyte is non-diffusively bound to the competitive binding portion.

The present invention further provides a method for detecting or determining an analyte in a test sample utilizing the test device of the invention. A solution containing the analyte and a conjugate of the analyte and liposomes encapsulating a detectable marker is contacted with a contact portion proximate to one end of the absorbent material of the test device. The test solution is allowed to traverse the absorbent material, via capillary action, from the contact portion through a measurement portion of the absorbent material which is positioned away from the end to which the contact portion is proximate. The measurement portion has a receptor for the analyte-liposome conjugate non-diffusively bound thereto. As described above, the absorbent material of the test device further includes a competitive binding portion between the contact and measurement portions, to which a binding material for the analyte is non-diffusively bound. After the test solution has traversed the absorbent material of the test device as described above, the amount of marker in the measurement portion of the absorbent material, i.e., either the absolute concentration, or the amount relative to some standard reference concentration(s), is determined as a measure of the analyte in the sample.

The invention further provides a method and device for determining an analyte in a test sample employing an automatic electrochemical signal production and amplification method. In this aspect, the test device comprises an absorbent material, having contact and competitive binding portions as described above. However, the measurement portion described above is replaced in this embodiment with an electrochemical measurement portion. The electrochemical measurement portion may be designed for either amperometric or potentiometric measurement.

For amperometric measurement, the electrochemical measurement portion has working, reference, and counter electrode portions, each of which is segregated from each other and from the other portions on the absorbent material. The working, reference, and counter electrodes are adapted for electrical connection with one another through an appropriate electrochemical analyzer. Of the three electrode portions, the working electrode portion is positioned most adjacent to the competitive binding portion, and the reference electrode portion is positioned between the working and counter electrode portions on the absorbent material. A liposome lysing agent is also non-diffusively bound to the absorbent material, either in the working electrode portion, or in a liposome lysing portion positioned between the competitive binding portion and the working electrode portion, and segregated from the competitive binding portion.

The present invention further provides a method for detecting or determining an analyte in a test sample utilizing a test device which relies on electrochemical detection of an electroactive marker. An electrolyte solution containing the analyte and a conjugate of the analyte and liposomes encapsulating an electroactive marker is contacted with a contact portion proximate to one end of the absorbent material of the test device. The test solution is allowed to traverse the absorbent material, via capillary action, from the contact portion, through an electrochemical measurement portion of the absorbent material which is positioned away from the end to which the contact portion is proximate. The electrochemical measurement portion includes working, reference, and counter electrode portions, each of which is segregated from each other and from the other portions on the absorbent material. The working electrode portion, as described above, is position most adjacent the competitive binding portion, with the reference electrode portion positioned between the working and counter electrode portions on the absorbent material. The absorbent material further has a liposome lysing agent non-diffusively bound to the absorbent material, either in the working electrode portion, or in a liposome lysing portion position between the competitive binding portion and the working electrode portion. The liposome lysing portion is segregated from the competitive binding portion. As the test solution traverses the absorbent material of the test device as described above, the flow of electrolyte test solution through the working electrode and reference electrode portions and into the counter electrode portion completes a circuit between the counter and working electrode portions, causing current to flow. Also, the liposomes come into contact with the liposome lysing agent, and lysis of the liposomes causes release of the electroactive marker. The current flowing between the counter and working electrode portions is then measured as a measure of the analyte in the sample.

A test device designed for potentiometric marker measurement is also provided in accordance with the invention. This test device is as described above, except that the electrochemical measurement portion has indicator electrode and reference electrode portions adapted for electrical contact with one another, wherein the indicator electrode portion is positioned between and segregated from the competitive binding portion and from the reference electrode on the absorbent material. A liposome lysing agent is also non-diffusively bound to the absorbent material, either in the indicator electrode portion, or in a liposome lysing portion which is positioned between the competitive binding portion and the indicator electrode portion, and which is segregated from the competitive binding portion.

A method for detecting or determining an analyte using such a test device is also provided in accordance with the invention. As before, an electrolyte solution containing the analyte and a conjugate of the analyte and liposomes encapsulating a electroactive marker is allowed to traverse the absorbent material from the contact portion through the electroactive measurement portion. As the electrolyte test solution flows through the indicator electrode portion into the reference electrode portion, a potential differential is set up between the two electrode portions. In addition, the liposomes are lysed by contact with the liposome lysing agent. The potential difference between the two electrodes is then measured as a measure of the analyte in a sample.

The device and method of the invention can be used directly in the field. The device is used only once, and, therefore, is free from residual environmental contaminants other than what may be present in the sample to be measured. Samples can be assayed within minutes after collection, with the results immediately available on-site. In addition, the device and method of the invention are much less complex than many of the prior materials and methods. For example, a visible dye can be used as the encapsulated marker, eliminating the need for any detection or measurement instrumentation, and a separate marker or indicator development step is not required with any embodiment of the invention. Also, marker-loaded liposomes as used in the device and method of the invention provide a highly sensitive, rapid or even instantaneous signal production/amplification system. Furthermore, the amount of liposome-encapsulated marker measured in the measurement portion of the absorbent material of the test device is directly proportional to the analyte concentration in the sample. This feature of the invention provides a particular advantage over prior test devices and immunoassays, providing an intuitive correlation between signal strength and analyte concentration.

DETAILED DESCRIPTION OF THE INVENTION

Figure 1:
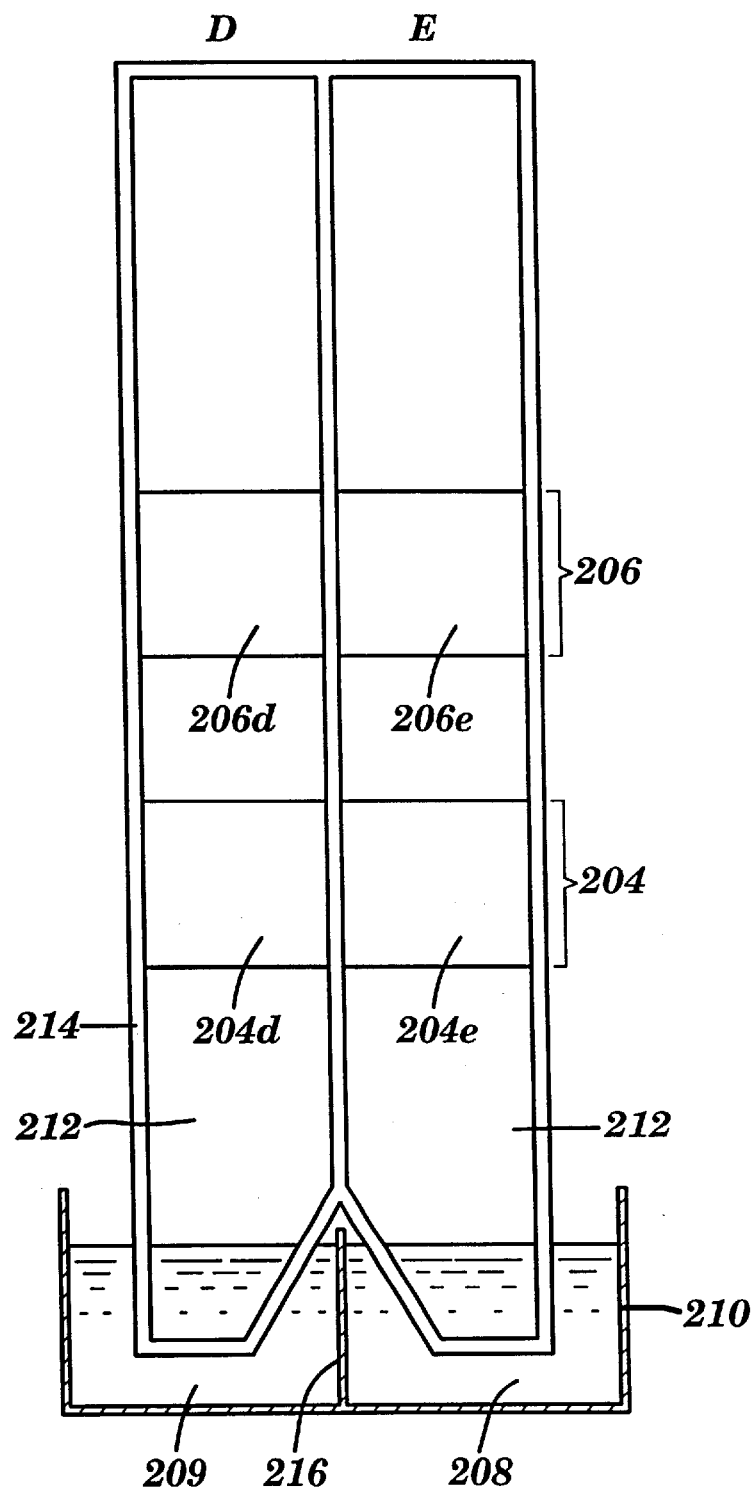
FIG. 1 is a schematic of a multiple channel test device in accordance with the invention.

As described above, the present invention is directed to a test device for detecting or determining an analyte in a test solution. The test device includes an absorbent material which comprises a contact portion proximate to a first end of the absorbent material for contact with and uptake of the test solution. The absorbent material of the test device further comprises a measurement portion at a location on the absorbent material which is positioned away from the first end. The measurement portion has a receptor for a conjugate of the analyte and liposomes non-diffusively bound thereto, wherein the liposomes have a detectable marker in the interior thereof. The test device also further comprises a competitive binding portion positioned between and segregated from the contact and measurement portions, which competitive binding portion has a binding material for the analyte non-diffusively bound thereto.

The invention is also directed to a method for detecting or determining an analyte, including the steps of providing a test device as described immediately above, contacting a solution of the analyte and the conjugate with the contact portion of the test device, allowing the solution to migrate from the contact portion through the measurement portion of the absorbent material, and determining the amount of the marker in the measurement portion as a measure of the analyte in a sample.

The invention further provides a method and device for determining an analyte in a test sample employing an automatic electrochemical signal production and amplification method. In this aspect, the test device comprises an absorbent material, having contact and competitive binding portions as described above. However, the measurement portion described above is replaced in this embodiment with an electrochemical measurement portion. The electrochemical measurement portion may be designed for either amperometric or potentiometric measurement.

For amperometric measurement, the electrochemical measurement portion has working, reference, and counter electrode portions, each of which is segregated from each other and from the other portions on the absorbent material. The working, reference, and counter electrodes are adapted for electrical contact with one another. Of the three electrode portions, the working electrode portion is positioned most adjacent to the competitive binding portion, and the reference electrode portion is positioned between the working and counter electrode portions on the absorbent material. A liposome lysing agent is also non-diffusively bound to the absorbent material, either in the working electrode portion, or in a liposome lysing portion positioned on the absorbent material between the competitive binding portion and the working electrode portion, and segregated from the competitive binding portion.

The present invention further provides a method for detecting or determining an analyte in a test sample utilizing a test device which relies on electrochemical (amperometric)

detection of an electroactive marker. An electrolyte solution containing the analyte and a conjugate of the analyte and liposomes encapsulating an electroactive marker is contacted with a contact portion proximate to one end of the absorbent material of the test device. The test solution is allowed to traverse the absorbent material, via capillary action, from the contact portion through an electrochemical measurement portion of the absorbent material which is positioned away from the end to which the contact portion is proximate. The electrochemical measurement portion includes working, reference, and counter electrode portions, each of which is segregated from each other and from the other portions on the absorbent material. The working electrode portion, as described above, is position most adjacent the competitive binding portion, with the reference electrode portion positioned between the working and counter electrode portions on the absorbent material. The absorbent material further has a liposome lysing agent non-diffusively bound to the absorbent material, either on the working electrode portion, or in a liposome lysing portion position between the competitive binding portion and the working electrode portion. The liposome lysing portion is segregated from the competitive binding portion. As the test solution traverses the absorbent material of the test device as described above, the flow of electrolyte test solution through the working electrode and reference electrode portions and into the counter electrode portion completes a circuit between the counter and working electrode portions, causing current to flow. Also, the liposomes come into contact with the liposome lysing agent, and lysis of the liposomes causes release of the electroactive marker. The current flowing between the counter and working electrode portions is then measured as a measure of the analyte in the sample.

A test device designed for potentiometric marker measurement is also provided in accordance with the invention. This test device is as described above, except that the electrochemical measurement portion has indicator electrode and reference electrode portions adapted for electrial connection with one another, wherein the indicator electrode portion is positioned between and segregated from the competitive binding portion and from the reference electrode on the absorbent material. A liposome lysing agent is also non-diffusively bound to the absorbent material, either in the indicator electrode portion, or in a liposome lysing portion which is positioned between the competitive binding portion and the indicator electrode portion, and which is segregated from the competitive binding portion.

A method for detecting or determining an analyte using such a test device is also provided in accordance with the invention. As before, an electrolyte solution containing the analyte and a conjugate of the analyte and liposomes encapsulating an electroactive marker is allowed to traverse the absorbent material through the electroactive measurement portion. As the electrolyte test solution flows through the indicator electrode portion into the reference electrode portion, a potential differential is established between the two electrode portions. In addition, the liposomes are lysed by contact with the liposome lysing agent. The potential difference between the two electrodes is then measured as a measure of the analyte in a sample.

By "analyte" is meant the compound or composition to be measured that is capable of binding specifically to an antibody, usually an antigen or hapten.

By "binding material" is meant an immunoglobulin or derivative or fragment thereof having an area on the surface or in a cavity which specifically binds to and is thereby defined as complementary with a particular spatial and polar organization of another molecule—in this case, the analyte. The binding material, such as an antibody, can be monoclonal or polyclonal and can be prepared by techniques that are well known in the art such as immunization of a host and collection of sera or hybrid cell line technology. The binding material may also be any naturally occurring or synthetic compound that specifically binds the analyte of interest.

By "receptor" is meant any compound or composition capable of recognizing a particular spatial and polar organization of a molecule, e.g., epitopic or determinant site. Illustrative receptors include naturally occurring receptors, e.g., egg white avidin, streptavidin thyroxine binding globulin, antibodies, Fab fragments, lectins, nucleic acids, protein A, protein G, and the like.

By "marker accumulating agent" is meant any ion, compound, or composition capable of trapping electroactive marker materials released from the liposome interiors. Ion-exchange resins are preferred marker accumulating agents in accordance with the invention.

By "absorbent material" is meant a porous material having a pore size of from 0.05 $\mu$m to 50 $\mu$m, preferably from 0.45 $\mu$m to 5 $\mu$m, which is susceptible to traversal by an aqueous medium in response to capillary force. Such materials may be natural polymeric materials, particularly cellulosic materials, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, activated nylon, etc.; either used by themselves or in conjunction with a support, as described below.

The absorbent material may be polyfunctional or be capable of being polyfunctionalized to permit covalent bonding of receptors or antibodies as well as to permit bonding of other compounds which form a part of the signal producing system.

The absorbent material which is employed in the test device and method of the invention is generally a cellulose ester with nitrocellulose giving exceptionally good results. It is to be understood that the term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Such materials, which are formed from cellulose esterified with nitric acid alone, or a mixture of nitric acid and another acid such as acetic acid, are often referred to as nitrocellulose paper.

Although nitrocellulose is a preferred material for producing the test device, it is to be understood that other materials, having a surface area sufficient for supporting the binding material in a concentration as hereinbelow described may also be employed for producing such test devices.

In general, the absorbent material which is used in the device and method of the invention has a surface area such that is capable of supporting the binding material in a concentration of at least 1 $\mu$g/cm$^2$, (most generally in a concentration of least 10 $\mu$g/cm$^2$) and preferably at least 40 $\mu$g/cm$^2$.

Absorbent materials having high surface areas (such as nitrocellulose) are particularly preferred in that the binding material may be supported on such materials in a high concentration. It is to be understood, however, that the concentration of binding material which is actually used is dependent in part on the binding affinity of the binding material. Accordingly, the scope of the invention is not limited to a particular concentration of binding material on the absorbent material.

Application of receptors, binding materials, liposome lysing agents, and marker accumulating agents to the absorbent material may be accomplished by well-known techniques, for example, by spraying or spotting a solution of those materials onto the absorbent material.

The amount of receptor which is bound to the absorbent material at the measurement portion will vary depending upon the amount required to bind the unbound conjugate to enable an effective assay. Generally, the amount of receptor at the measurement portion will be at least 10 $\mu g/cm^2$.

The receptor and the binding material and, where desired, members of the signal producing system, can be bound to the absorbent material by adsorption, rather 15 than covalent bonding, as long as such binding is non-diffusive. This will involve contacting the absorbent material with a solution containing the materials to be bound to the material and allowing the material to dry. In general, this procedure will be useful only where the absorbent material is relatively hydrophobic or has a high surface charge, and subsequent treatment with proteins, detergents, polysaccharides, or other materials capable of blocking non-specific binding sites will be required.

After application of the binding material to the competitive binding portion on the absorbent material, the residual binding capacity of the absorbent material is saturated or blocked with one or more types of proteins or other compounds such as polyvinylpyrrolidone, polyvinylalcohol, etc. which do not specifically bind the materials to be employed in the assay. Thus, for example, the residual binding capacity of the substrate may be blocked so as to prevent non-specific binding by the use of bovine serum albumin, as described in Towbin, et al., *Proc. Nat'l. Acad. Sci.*, 76 (1979) 4350, which is hereby incorporated by reference. The techniques for preventing non-specific binding are generally known in the art, and such techniques are also generally applicable to preventing non-specific binding in the assay of the present invention. Examples of particularly suitable techniques for blocking with polyvinylpyrrolidone and polyvinylalcohol are described, for example, Bartles, et al. *Anal. Biochem.*, 140 (1984) 784, and in British Patent Specification GB 2204398 A, respectively, which are hereby incorporated by reference.

In conjunction with a blocking agent, a surfactant may be applied to the absorbent material in a concentration sufficient to facilitate migration of the analyte-liposome conjugate without lysis of the liposomes.

The absorbent material can be a single structure such as a sheet cut into strips. The absorbent material can be mounted on a support material. On the other hand, the absorbent material may provide its own support. In one embodiment of the invention, the test device is a strip of particulate material bound to a support or solid surface such as found, for example, in thin-layer chromatography. The absorbent material can be a sheet having lanes thereon, or be a uniform sheet capable of division into separate lanes by physical removal of the absorbent material from the support to induce lane formation, wherein a separate assay can be performed in each lane as shown in FIGS. 1–3 and 6–7. The absorbent material can have a shape that is rectangular, circular, oval, triagonal, or the like, provided that there is at least one direction of traversal of a test solution by capillary migration. Other directions of traversal may occur such as in an oval or circular piece contacted in the center with the test solution. However, the main consideration is that there be one direction of flow from the contact portion through the measurement portion. In this discussion strips of absorbent material are described by way of illustration and not limitation.

FIG. 1 is a schematic of a test device in accordance with the invention, depicted immediately after insertion into control solution 209 and test solution 208, which are held in tray 210 having partition 216 extending across the entire width of tray 210 to divide tray 210 into separate compartments for the control and test solutions. As shown in FIG. 1, absorbent material 212 is mounted on support 214. The test device shown in FIG. 1 is divided into two channels, namely, control channel D and test channel E, and competitive binding portions 204 and measurement portions 206. Control channel D includes competitive binding portion 204d, which has a binding material for the analyte of interest non-diffusively bound thereto. Control channel D further includes measurement portion 206d, which, as described above, has a receptor for the appropriate analyte-liposome conjugate non-diffusively bound thereto. Test channel E similarly has competitive binding portion 204e and measurement portion 206e, which have been constructed to recognize and bind the analyte and the analyte-liposome conjugate, respectively, as described above.

According to the embodiment of the invention shown in FIG. 1, the contact portion of each channel of the test strip is the end of the strip to be inserted into the test or control solutions.

Test solution 208 is typically prepared, as described below, by combining a sample known or suspected to contain the analyte with the analyte-liposome conjugate in an aqueous medium. In accordance with the embodiment shown in FIG. 1, control solution 209 is similarly prepared to have the same concentration of the conjugate as test solution 208, and a known concentration of analyte.

In use, the contact portion of absorbent material 212 of control channel D is inserted into control solution 209, while the contact portion of absorbent material 212 of test channel E is inserted into test solution 208. Wetting of absorbent material 212 by capillary action is allowed to continue at least until measurement portions 206d and 206e are wet with control solution 209 and test solution 208, respectively. As control solution 209 and test solution 208 traverse channels D and E through competitive binding portions 204d and 204e, the analyte in control solution 209 and test solution 208 competes with the analyte-liposome conjugate in each of the solutions for available binding sites on the specific binding material bound to competitive binding portions 204d and 204e. Control solution 209 and test solution 208 continue to traverse channels D and E of the test device into and through measurement portions 206d and 206e, where the conjugate is trapped and accumulated in measurement portions 206d and 206e by the specific conjugate receptor bound thereto.

As is described below, qualitative measurement of the marker in measurement zones 206d and 206e may be made visually when the marker is a visible dye. Alternatively, the intensity of the color in measurement portions 206d and 206e may be visually compared with a series of reference standards, such as in a color chart, for a semi-quantitative determination of the amount of analyte in the sample. Other types of markers, as described below, may be detected and measured and using instrumentation such as a spectrophotometer or fluorimeter.

Figure 2:
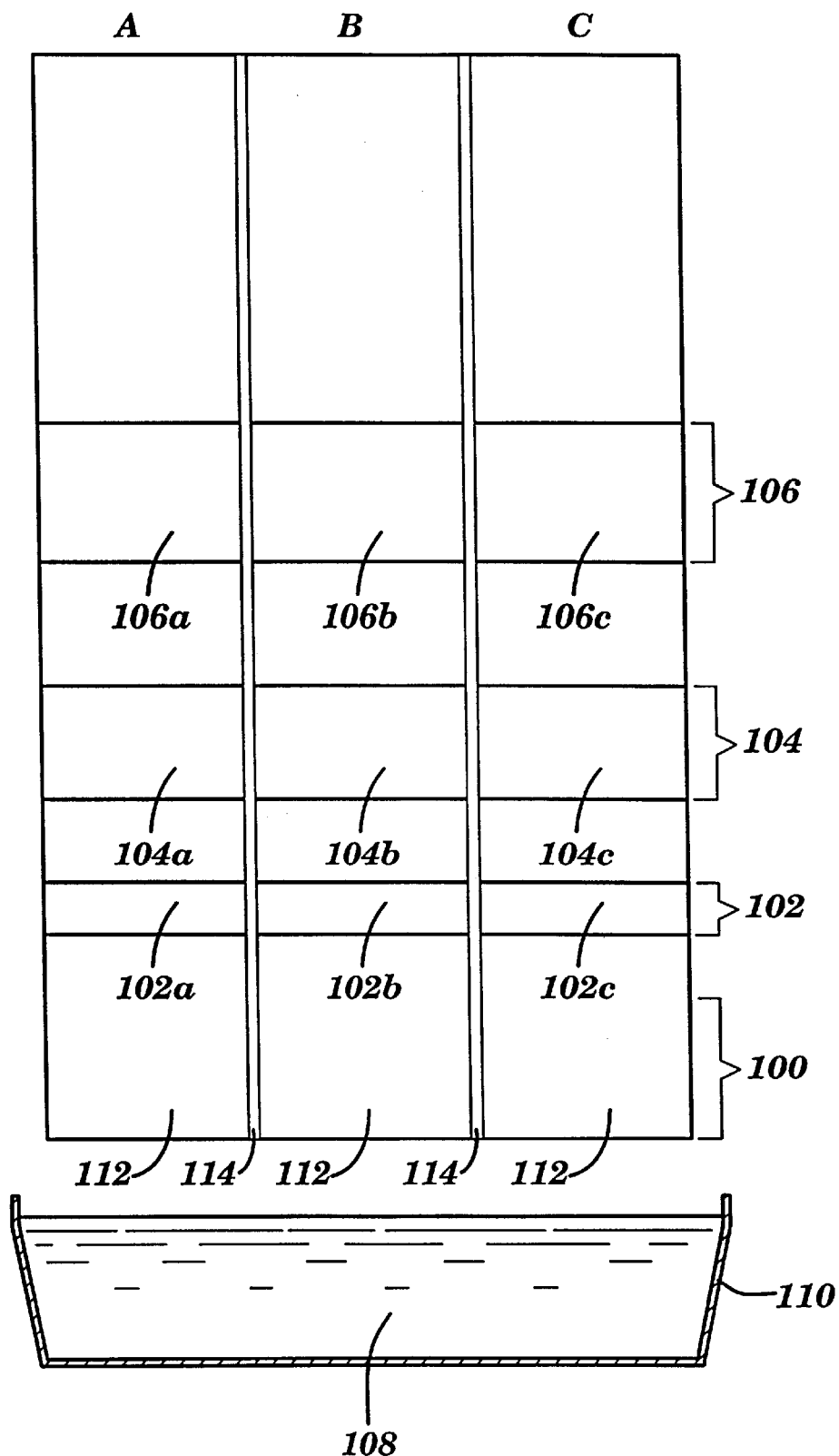
FIG. 2 is a schematic of an alternative multiple channel test device in accordance with the invention.

An alternative multiple channel test device in accordance with the invention is shown schematically in FIG. 2. In this case, the test device is shown before insertion into sample compartment 110 containing a wicking reagent such as carrier solution 108, which is generally a buffered saline solution. In the embodiment shown in FIG. 2, the test device is divided into high control channel A, test channel B, and low control channel C. As was described above in connection with FIG. 1, absorbent material 112 is supported on support 114. The test device includes wicking portions 100, contact portions 102, competitive binding portions 104, and measurement portions 106. High control channel A includes contact portion 102a, competitive binding portion 104a, and measurement portion 106a. Test channel B similarly includes contact portion 102b, competitive binding portion 104b, and measurement portion 106b. Finally, low control channel C includes contact portion 102c, competitive binding portion 104c, and measurement portion 106c.

The test device shown schematically in FIG. 2 is designed for the simultaneous measurement of the analyte in a test sample and high- and low-level control compositions to provide linear interpolation and verification of response. A high-level control solution, the test solution, and a low-level control solution are spotted onto contact portions 102a, 102b, and 102c, respectively, prior to insertion of the test device into carrier solution 108, which includes the analyte-liposome conjugate. Following migration of carrier solution 108 through contact portions 102a, 102b, and 102c, competitive binding portions 104a, 104b, and 104c, and measurement portions 106a, 106b, and 106c and, optionally, to the end of channels A, B and C, color intensity or other marker signal is observed or quantified in measurement zones 106a, 106b, and 106c which, as described above in connection with FIG. 1, each have the receptor for the analyte-liposome conjugate non-diffusively bound thereto.

As was also described in connection with FIG. 1, the analyte in each of the high- and low-level control solutions, and the test solution, and the analyte-liposome conjugate in the carrier solution, compete for available binding sites on the binding material, which is non-diffusively bound to competitive binding portions 104a, 104c, and 104b, respectively.

The support for the absorbent material where a support is desired or necessary will normally be hydrophobic, water insoluble, non-porous, and rigid, and usually will be of the same length and width as the absorbent strip but may be larger or smaller. A wide variety of organic and inorganic materials, both natural and synthetic, and combinations thereof, may be employed, provided only that the support does not interfere with the production of signal from the marker. Illustrative polymers include polyethylene, polypropylene, poly(4 -methylbutene), polystyrene, polymethacrylate, poly(ethylene terephthalate), nylon poly (vinyl butyrate), glass, ceramics, metals, and the like.

The size of the piece of absorbent material is dependent on several considerations. The primary consideration is to separate unbound conjugate from bound conjugate and to capture unbound conjugate at the measurement portion to give a sufficient signal so that a sensitive and accurate assay is achieved. The following discussion is primarily focused on strips of absorbent material for purpose of illustration and not limitation. As mentioned above, other shapes such as circular, oval, triagonal, and the like, fall equally within the scope of this invention. The dimensions thereof and other parameters can be determined by those skilled in the art with reference to the disclosure herein.

When capillary flow is predominantly upward, the length and thickness of the strip control the amount of solution that can pass through the measurement portion. If the transfer of a large volume of test solution is desired, the fluid capacity of the strip above the measurement portion must be sufficient to accommodate the desired volume. Alternatively, an absorbing pad may be used to contact the end of the strip opposite the end used to contact the test solution.

To permit conservation of reagents and provide for samples of limited size, the width of the strip will generally be relatively narrow, usually less than 20 mm preferably less than 10 mm. Generally, the width of the strip will not be less than about 2 mm and will usually range from about 2 mm to 10 mm, preferably from about 3 mm to 6 mm.

As is described in detail below, the test device in accordance with the invention may be modified for simultaneous multiple analyte detection or determination. The length of the strip will depend on the concentration of the analyte and practical considerations such as ease of handling and the number of measurement portions on the strip and will be about 4 cm to 20 cm, usually about 5 cm to 15 cm, preferably about 6 to 13 cm but may be of any practical length. The structure of the strip can be varied widely and includes fine, medium fine, medium, medium coarse and coarse. In general, smaller pore size and finer material will provide slow capillary flow and more efficient capture of bound conjugate on the strip. Courser, more porous materials provide faster flow, but the efficiency of capture is reduced. Selection of the porosity of the material depends on the rate of binding of the components for a given assay.

The position of the competitive binding portion, and measurement portion (or portions, where a plurality of analytes are being determined), should be governed by the basic principle involved in the present invention. One desires to pass by capillarity a sufficient amount of the test solution through the strip to the measurement portion to separate bound conjugate from unbound conjugate and to bind the unbound conjugate at the measurement portion to produce a signal that is detectable. It is desirable to position the measurement portion close to the competitive binding portion. Desirably, the measurement portion should be at least 3 mm, preferably at least 8 mm, from the competitive binding portion of the strip. The measurement portion should be positioned on the absorbent material so as to enable the test solution to pass through the measurement portion by capillary action so as to capture the unbound conjugate. Generally, the distance between the competitive binding portion and the contact portion should be at least 2 mm, preferably at least 5 mm. Where several measurement portions are used for multi-analyte determinations, the measurement portions can be grouped close together or apart but must not be so close as to compromise resolution of the signals. Consequently, such measurement portions usually should be spaced not less than 0.5 mm apart, preferably at least 1 mm apart.

In carrying out the method of the invention, the protocol will normally involve combining the sample suspected of containing the analyte with the conjugate in an aqueous medium to form the aqueous test solution. The sample may be derived from a wide variety of sources, such as physiologic fluids, illustrated by saliva, serum, plasma, urine, ocular lens fluid, spinal fluid, etc., chemical processing streams, food, waste water, natural waters, soil extracts, etc. Various addenda may be added to adjust the properties of the test solution, or of a carrier solution used as a wicking reagent, depending upon the properties of the other components of the device, as well as on those of the liposomes or the analyte-liposome conjugate, or the analyte itself. Examples of solution addenda which may be incorporated into test, control, or carrier solutions in accordance with the invention include buffers, and sample or analyte solubilizing agents, such as, for example, nonpolar solvents.

The contact portion of the absorbent material, which usually includes the end of the absorbent material to which the contact portion is proximate, is contacted with test solution, usually by immersion of the contact portion into the test solution. Wetting of the absorbent material by capillary action is allowed to continue at least until the measurement portion is wet.

Alternatively, the test solution may be contacted with the absorbent material by spotting the test solution onto the absorbent material in the contact portion. In this case, the contact portion includes a wicking portion at the first end of the absorbent material. In use, the wicking portion of the contact portion is inserted into a wicking reagent after the test solution is spotted onto the contact portion, outside of the wicking portion.

For the most part, relatively short times are involved for the test solution to traverse the strip. Usually, traversal of the test solution over the strip will take at least 30 seconds and not more than ½ hour, more usually from about 1 minute to 10 minutes. In accordance with the method of the invention, the signal is rapidly, even immediately, detectable.

The conjugate of the analyte and the marker-encapsulating liposome may be prepared by procedures generally known in the art, with the particular procedure used in a given case being dependent upon the analyte which is employed. Such techniques include covalent coupling, derivatization or activation, and the like. The liposomes may be produced from a component which has been derivatized with the analyte, whereby the liposomes, when produced, are conjugated with the analyte. In another procedure, the liposomes, including the marker, may be initially formed, followed by conjugating the liposomes with analyte by procedures known in the art.

Liposomes can be prepared from a wide variety of lipids, including phospholipids, glycolipids, steroids, relatively long chain alkyl esters; e.g., alkyl phosphates, fatty acid esters; e.g. lecithin, fatty amines, and the like. A mixture of fatty materials may be employed, such as a combination of neutral steroid, a charge amphiphile and a phospholipid. Illustrative examples of phospholipids include lecithin, sphingomyelin, and dipalmitoylphosphatidylcholine, etc. Representative steroids include cholesterol, chlorestanol, lanosterol, and the like. Representative charge amphiphilic compounds generally contain from 12 to 30 carbon atoms. Mono- or dialkyl phosphate esters, or alkyamines; e.g. dicetyl phosphate, stearyl amine, hexadecyl amine, dilaurylphosphate, and the like are representative.

The liposome sacs are prepared in aqueous solution containing the marker whereby the sacs will include the marker in their interiors. The liposome sacs may be prepared by vigorous agitation in the solution, followed by removal of the unencapsulated marker. Further details with respect to the preparation of liposomes are set forth in U.S. Pat. No. 4,342,826 and PCT International Publication No. WO80/01515, both of which are incorporated by reference.

As hereinabove indicated, the signal producing system includes a marker included in the interior of the conjugated liposomes. Suitable markers include fluorescent dyes, visible dyes, bio- and chemiluminescent materials, enzymatic substrates, and radioactive materials. Visible dyes and radioactive materials can be measured without lysis of the liposomes. However, even when liposome lysis is required, as when the other marker materials are used, a separate lysing step is not necessary, because a liposome lysing agent may be non-diffusively bound directly to the absorbent material as, for example, in the measurement zone. Suitable liposome lysing materials include surfactants such as octylglucopyranoside, sodium dioxycholate, sodium dodicylsulfonate, polyoxyethylenesorbitan monolaurate sold by Sigma under the trademark Tween-20, and a non-ionic surfactant sold by Sigma under the trademark Triton X-100, which is t-octylphenoxypolyethoxyethanol. Alternatively, complement lysis of liposomes may be employed.

A qualitative or semi-quantitative measurement of the presence or amount of an analyte of interest may be made with the unaided eye when visible dyes are used as the marker. Alternatively, when greater precision is desired, or when the marker used necessitates instrumental analysis, the intensity of the marker may be measured directly on the absorbent material using a quantitative instrument such as a fluorimeter, spectrophotometer, etc.

In one embodiment of the invention, a marker which is visible under the assay conditions is used so that the presence and/or amount of analyte may be determined without further treatment and without the use of instrumentation, e.g., by use of a liposome containing a dye as the marker.

In the method of the invention, a conjugate of the analyte and marker-loaded liposomes label are combined in an aqueous medium with a sample suspected of containing the analyte, to provide an aqueous test solution. Alternatively, the combination of the conjugate and the sample suspected of containing the analyte can take place on the absorbent material. The primary consideration is that a test solution containing the sample come in contact with a conjugate of the analyte and the marker-loaded liposomes prior to or at the contact portion of the absorbent material. A receptor capable of binding to the conjugate is non-diffusively bound to the absorbent material at the measurement portion. The binding material is non-diffusively bound to the absorbent material between the measurement portion and the contact portion. The contact portion of the absorbent material is contacted with the test solution, which will traverse the absorbent material through capillary action. This transversal can be upward, downward, horizontal or combinations thereof. The amount of the conjugate that becomes bound to the measurement portion through binding to the receptor is related to the amount of analyte in the sample. The signal producing system provides a detectable signal at the measurement portion only when the conjugate is bound to the receptor in the measurement portion, so that the presence of the analyte may be determined by detecting the signal at the measurement portion. Binding of the conjugate to the receptor may occur directly to a binding site on the liposome.

The present invention provides for an immunoseparation of bound conjugate from unbound conjugate. This is accomplished by having the binding material receptor non-diffusively bound to the absorbent material in the competitive binding portion between the measurement portion and the contact portion. A binding material will normally be chosen that provides for direct binding to the analyte. Usually, the binding material will be present in an amount that will provide the appropriate sensitivity required for a specific analyte.

The movement of the test solution along the absorbent material is due to capillary action. This capillary movement along the absorbent material causes the test solution to be carried to and through the measurement portion.

Measurement of the marker-loaded liposomes takes place in the measurement portion of the absorbent material. As described above, concentration or accumulation of the conjugate may be achieved by various immunospecific binding reactions as described above.

In one embodiment of the invention, the conjugate of the analyte and the liposomes is further bound to biotin. The assay is carried out in the same way but the receptor is anti-biotin such as avidin or antibody for biotin. When analyte is present, some biotinylated conjugate reaches the measurement portion and is bound by the anti-biotin or avidin. However, it has been found that egg white avidin, with the carbohydrate moiety still attached, strongly binds all of the liposomes, without the need of conjugating biotin to them. As the specificity of the assay lies in the immunorecognition reaction in the antibody zone, an avidin collection zone provides a simple solution to give the desired direct readout measurement.

In an electrochemical detection method, an electroactive species, such as ferrocyanide, is encapsulated into the liposomes. Electrodes are printed onto the strip, or the strip is placed in contact with the electrodes. After lysis of the liposomes, the quantity of the electroactive species is determined amperometrically or potentiometrically.

Figure 3:
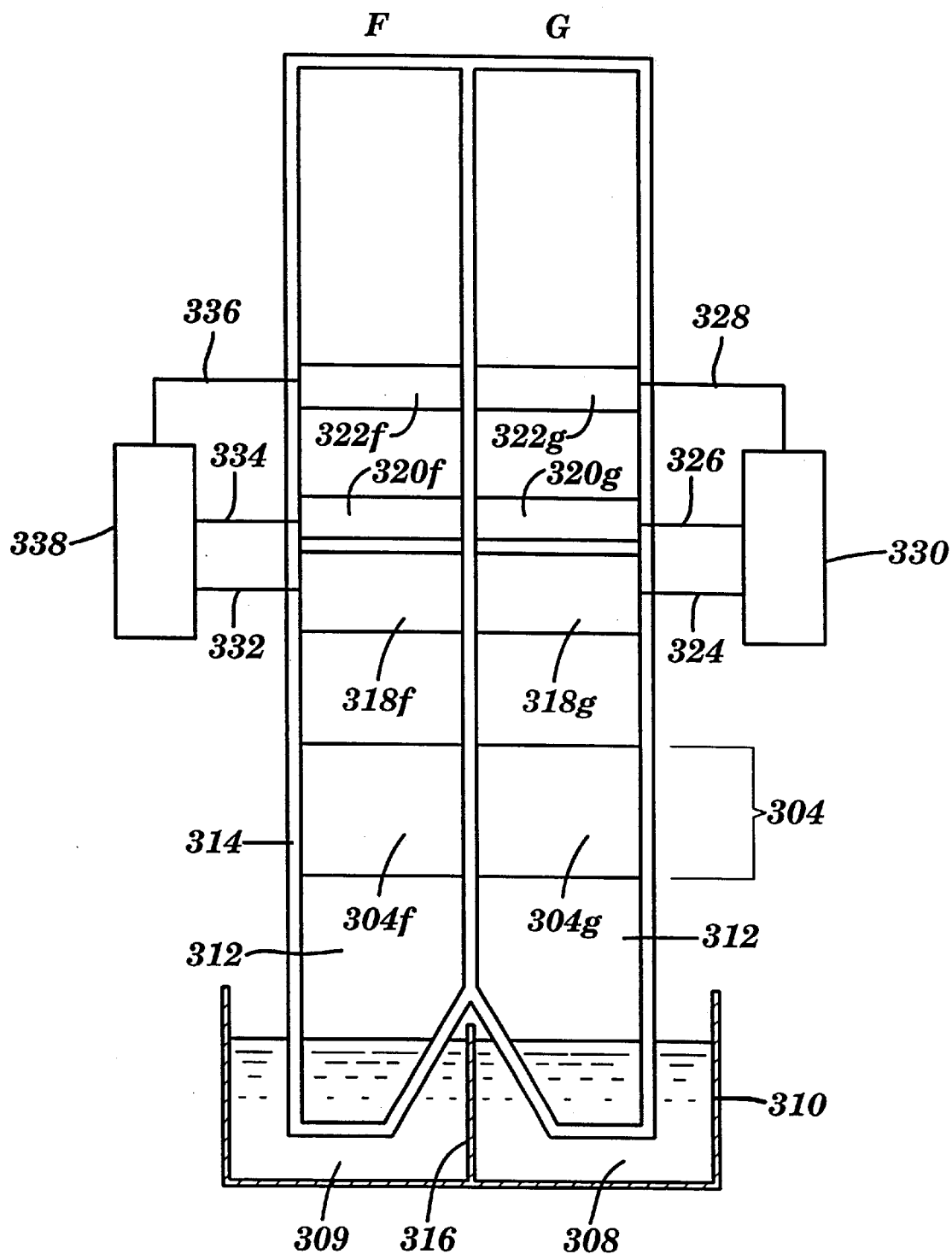
FIG. 3 is a schematic of the test device of FIG. 1, modified for electrochemical detection or determination of an analyte.

FIG. 3 is a schematic of a test device in accordance with the invention which employs electrochemical detection or measurement of an electroactive marker. The device in FIG. 3 is shown immediately after insertion into control solution 309 and test solution 308, which are kept separated from one another by partition 316 in tray 310. As was described above in connection with FIG. 1, the device is divided into control channel F and test channel G and includes absorbent material 312 mounted on support 314. As is the case with the device shown in FIGS. 1 and 2, competitive binding portion 304$f$ on absorbent material 312 in control channel F and competitive binding portion 304$g$ on absorbent material 312 in test channel G are substantially identical to one another prior to contact of control solution 309 and test solution 308 with those portions, respectively. Each of the competitive binding portions has the same binding material for the analyte of interest non-diffusively bound thereto. The test device shown in FIG. 3 further includes working electrode portions 318$f$ and 318$g$ for control channel F and test channel G, respectively. Reference electrode portions 320$f$ and 320$g$ and counter electrode portions 322$f$ and 322$g$ are also included on absorbent material 312 of the test device, as shown in FIG. 3.

Other than the working, reference, and counter electrode portions shown in FIG. 3, the test device is constructed as described above in connection with FIGS. 1 and 2. Each of the electrode portions is separated from the others on the absorbent material. Working electrode portion 318$f$, reference electrode portion 320$f$, and counter electrode portion 322$f$ are each adapted for electrical connection to one another via connections 332, 334, and 336, respectively, to potentiostat 338. Working electrode portion 318$g$, reference electrode portion 320$g$, and counter electrode portion 322$g$ are similarly each adapted for electrical connection to one another via connections 324, 326, and 328, respectively, to potentiostat 330. In operation, the working, reference, and counter electrode portions 318$g$, 320$g$, and 322$g$ of channel G are in electrical contact with one another, as is the case with reference electrode and working electrode portions 318$f$, 320$f$, and 322$f$ on channel F.

Reference electrodes 320$f$ and 320$g$ will usually be silver electrodes, while working electrode portions 318$f$ and 318$g$, and counter electrode portions 322$f$ and 322$g$ may be prepared from any suitable materials such as the noble metals, other metals such copper and zinc, or carbon electrode materials in various forms, including graphitic, glassy and reticulated carbon materials. Counter electrodes 322$f$ and 322$g$ may be composed of the same or a different material from working electrodes 318$f$ or 318$g$.

Each of the electrode portions shown in FIG. 3 may be prepared by screen printing of the electrode materials onto absorbent material 312. As is well known, screen printing involves preparation of an organic or aqueous slurry of the electrode material, typically, a fine powder of carbon, gold, etc., followed by application of the slurry across and through a silk screen onto the absorbent material of the test device. This slurry may optionally include a polymeric binder which aids in aggregating the fine metallic particles together on the surface of the absorbent material. The electrode material slurry may be fixed on the surface of the absorbent material by heating, however, the printed electrode portions are preferably allowed to air dry on the surface of the absorbent material.

The test device shown in FIG. 3 is designed for amperometric detection or quantification of an electroactive marker included in the interior of the liposomes included in the analyte-liposome conjugate incorporated in control solution 309 and test solution 308. Following insertion of the test device into control solution 309 and test solution 308, as shown in FIG. 3, and as described above in connection with FIG. 1, the control and test solutions are allowed to traverse the device, from the contact portions of both channels, through counter electrode portions 322$f$ and 322$g$. Competitive binding between the analyte and analyte-liposome conjugate occurs in competitive binding portions 304.

In the embodiment of the invention shown in FIG. 3, working electrode portions 318$f$ and 318$g$ include a marker accumulating agent, such as anion-exchange polymer, non-diffusively bound thereto. Working electrode portions 318$f$ and 318$g$ further incorporate a liposome lysing agent, as defined above, in an amount sufficient to lyse all of the liposomes contacting the lysing agent. Alternatively, the liposome lysing agent may be non-diffusively bound to absorbent material 312 in liposome lysing portions (not shown) located on absorbent material 312 in each of channels F and G between competitive binding portion 304$f$ and working electrode portion 318$f$ in channel F, and between competitive binding portion 304$g$ and working electrode portion 318$g$ on channel G. The liposome lysing portions must be separate from competitive binding portions 304$f$ and 304$g$ on absorbent material 312.

As control solution 309 and test solution 308, which are electrolyte solutions such as saline solutions of the analyte and analyte-liposome conjugate, traverse channels F and G of the test device through working electrode portions 318$f$ and 318$g$, the liposomes in the conjugate are lysed immediately before contact with or upon entry into working electrode portions 318$f$ and 318$g$ to release an electroactive marker substance included in their interiors. Electroactive markers are materials capable of undergoing oxidation or reduction. Suitable electroactive markers include metal ions, and organic compounds such as ascorbate, ascorbic acid, quinones, phenols, NADH. Ferrocyanide is the most preferred electroactive marker in accordance with the invention.

The electroactive marker released from the interior of the liposomes incorporated in the analyte-liposome conjugates in control solution 309 and test solution 308 are then accumulated by the ion-exchange material bound to working electrode portions 318$f$ and 318$g$ throughout the period during which the control and test electrolyte solutions migrate past reference electrode portions 320f and 320g to counter electrode portions 322f and 322g. At that point, the electrical circuits between the working, reference, and counter electrode portions of each of channels F and G is automatically completed and electrolysis of the accumulated electroactive marker occurs. The current flowing through the circuits, which is directly proportional to the amount of marker released by the liposomes, and corresponds to the amount of analyte in the sample, is then measured by potentiostat 330. Devices which may be used as potentiostats in accordance with the invention include the Cypress System Electrochemical Analyzer and the BAS Electrochemical Analyzer.

Figure 6:
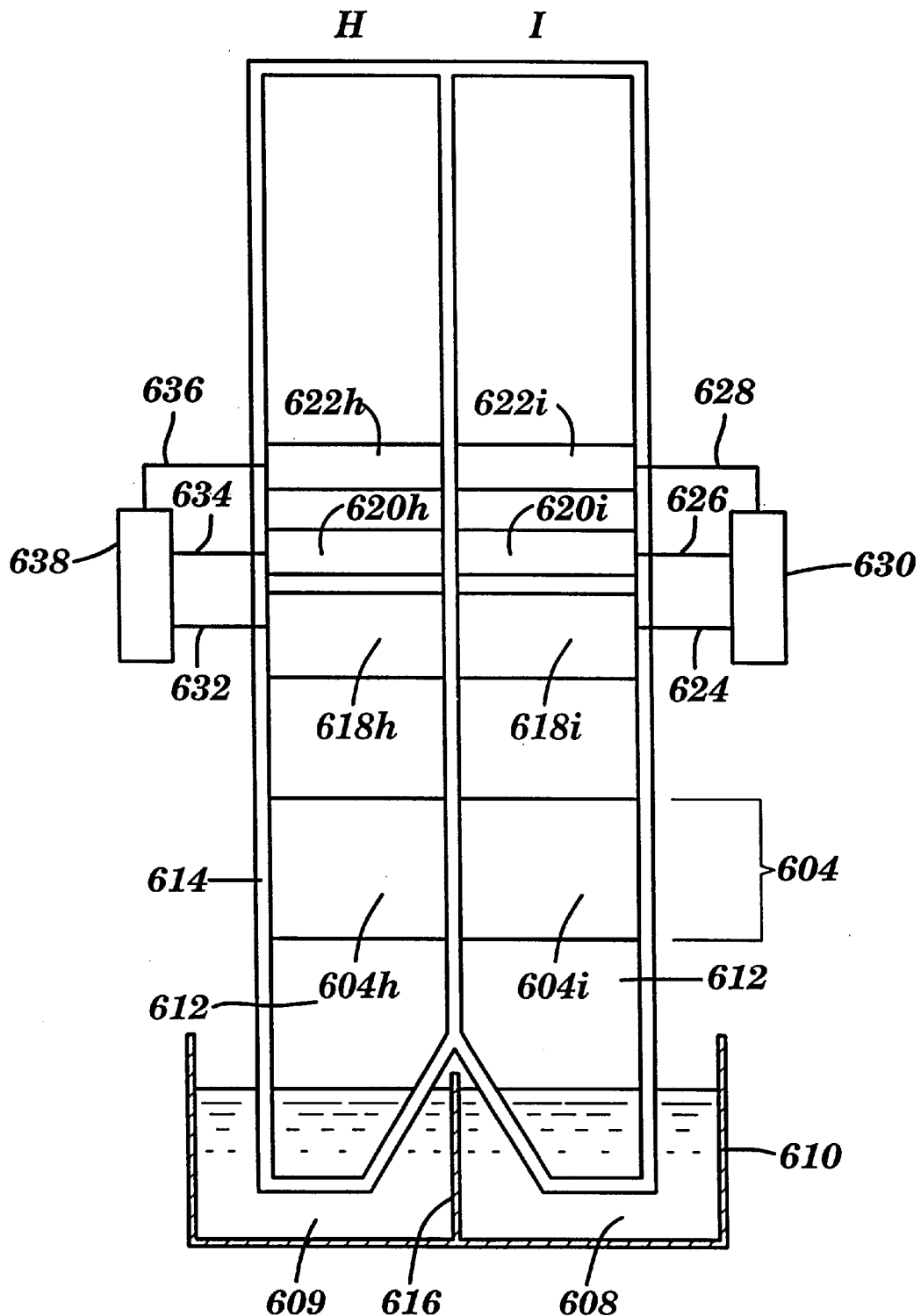
FIG. 6 is a schematic of an alternatively modified electrochemical test device.

An alternative design for a test device constructed for electrochemical detection or quantification of a liposome-encapsulated electroactive marker is shown schematically in FIG. 6. Electrolyte control solution 609 and electrolyte test solution 608, separated by a partition 616 in tray 610, are as described above in connection with the corresponding features shown in FIG. 3. Similarly, the test device shown in FIG. 6, comprising control channel H and test channel I, each of which comprises absorbent material 612 mounted on support 614, and each of which has comparative binding portions 604, are as described above for the corresponding structures described above in connection with FIG. 3. The device shown in FIG. 6 further includes working electrode portions 618h and 618i, reference electrode portions 620h and 620i, and counter electrode portions 622h and 622i, which are separated from one another on absorbent material 612. Working electrode portion 618h is adapted for electrical connection to potentiostat 638, and through potentiostat 638 to reference electrode portion 620h and counter electrode portion 622h, via connection 632. Working electrode portion 618i is similarly adapted for electrical connection to potentiostat 630, and through potentiostat 630 to reference electrode portion 620i and counter electrode portion 622i, via connection 624. Similarly, reference electrode portions 620h and 620i, and counter electrode portions 622h and 622i, are adapted for electrical connection through connections 634 and 626, and through connections 636 and 628, respectively, to potentiostats 638 and 630.

The test device shown in FIG. 6 further incorporates a liposome lysing agent non-diffusively bound to a absorbent material 612, either in working electrode portions 618h and 618i, or, alternatively, in separate liposome lysing portions (not shown) on absorbent material 612 in each of channels H and I between competitive binding portion 604h and working electrode portion 618h, on control channel H, and between competitive binding portion 604i and working electrode portion 618i on absorbent material 612 of test channel I. As in the case of the device shown in FIG. 3, the separate liposome lysing portions must be separated from competitive binding portions 604h and 604i on absorbent material 612 in each of channels H and I. However, it is not necessary that the liposome lysing portion be separated from working electrode portions 618h and 618i.

In contrast to the device shown in FIG. 3, the device shown in FIG. 6 does not include a marker accumulating agent in working electrode portions 618h and 618i. In operation, traversal of the test device by electrolyte control solution 609 and electrolyte test solution 610 proceeds as described previously in connection with FIG. 3 through working electrode portions 618h and 618i, reference electrode portions 620h and 620i, and counter electrode portions 622h and 622i, however, electroactive marker released as a result of contact between the analyte-liposome conjugate and the liposome lysing agent incorporated on absorbent material 612 in each of control channel H and test channel I is not accumulated in working electrode portions 618h and 618i. In this embodiment of the invention, once the electrical circuits between counter electrode portions 622h and 622i, and working electrodes 618h and 618i are completed, electrolysis of the released electroactive marker occurs continuously as the marker flows past working electrode portions 618h and 618i. The current measured by potentiostats 630 and 638 is then integrated for a fixed period of time to provide a measure of the amount of analyte in test solution 608.

Figure 7:
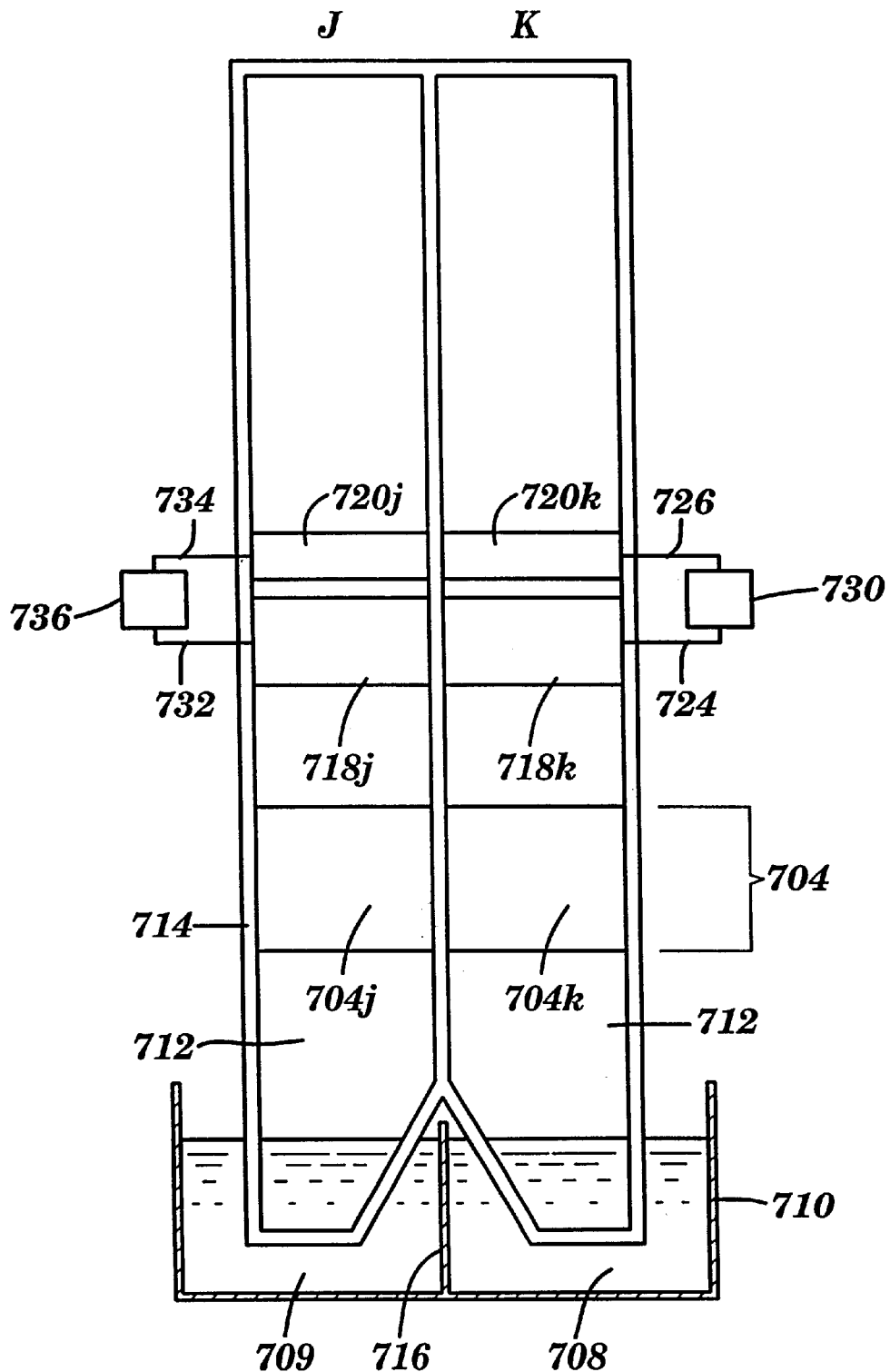
FIG. 7 is a schematic of yet another test device suitable for electrochemical detection or determination of an analyte.

Yet another embodiment of the test device of the present invention employ electrochemical detection is shown schematically in FIG. 7. In this case however, the potentiometric measurement of an electroactive marker released from the interior of the liposomes comprising the analyte-liposome conjugate is made. As was the case with the device shown in FIG. 6, electrolyte control solution 709 and electrolyte test solution 708 are kept separated by partition 716 in tray 710. The test device shown in FIG. 7 is constructed as was described above in connection with FIGS. 3 and 6, and includes control channel J and test channel K, each comprising absorbent material 712 mounted on support 714. As was the case with FIGS. 1, 3, and 6 described above, the device in FIG. 7 is shown immediately after insertion of the contact portion of each of channels J and K into control solution 709 and test solution 708, respectively.

The device shown in FIG. 7 further includes competitive binding portions 704. In the case of the test device shown FIG. 7, however, the device comprises indicator electrode portions 718j and 718k, and reference electrode portions 720j and 720k, which electrode portions are separated from one another on absorbent material 712, as shown in FIG. 7. Indicator electrode portions 718j and 718k, and reference electrode portions 720j and 720k are adapted for electrical connection to potentiometers 736 and 730 through connections 732 and 724, respectively, for indicator electrode portions 718j and 718k, and 734 and 726, respectively, for reference electrode portions 720j and 720k.

As was described above in connection with FIG. 3, reference electrode portions 720j and 720k may be prepared, as described above, by screen printing a slurry of finely divided silver powder onto absorbent material 712. Indicator electrode portions 718j and 718k may be prepared in the same way from any of the electrode materials described above in connection with working electrode portions 318f and 318g and counter electrode portions 322f and 322g, of FIG. 3.

It is necessary to incorporate a liposome lysing agent on absorbent material 712 of the test device shown in FIG. 7 between competitive binding portion 704j and reference electrode portion 720j of channel J and between competitive binding portion 704k and reference electrode portion 720k of channel K. However, as was described above in connection with FIGS. 3 and 6, the liposome lysing agent may either be non-diffusively bound to absorbent material 712 in indicator electrode portions 718j and 718k, or may it be bound to a separate liposome lysing portion located on absorbent material 712 between competitive binding portion 704j and indicator electrode portion 718j in channel J, and between competitive binding portion 704k and indicator electrode portion 718k in channel K. As before, it is necessary that such liposome lysing portions be separated from competitive binding portions 704 on absorbing material 712 in channels J and K.

Traversal of channel J by electrolyte control solution 709 and simultaneous traversal of channel K by electrolyte test solution 708, from the contact portions of channels J and K through competitive binding portions 704, which, as described above, have a binding material for the analyte of interest non-diffusively bound thereto, proceeds as described above in connection with FIGS. 3 and 6. As control solution 709 and test solution 708 migrate through indicator electrode portions 718j and 718k into reference electrode portions 720j and 720k, a potential differential is set up between the indicator and reference electrode portions in each channel. These potential differentials are measured by potentiometers 736 and 730, which may be pH meters, such as those available from Orion, Corning, or Beckman. The potential differentials are directly proportional to the concentrations of the electroactive markers released from the liposome interiors, and correspond to the concentrations of the analyte in the control and test solutions.

It should be noted that although the working, counter, and reference electrode portions in FIGS. 3 and 6, and the reference and indicator electrodes in FIG. 7 have been shown in specific positions, the positions can be otherwise than shown. Specifically, for example, the relative positions of the reference and working electrode portions in FIGS. 3 and 6 may be reversed. Similarly, the positions of the reference and indicator electrodes shown in FIG. 7 may be reversed. Although the counter electrode portions in FIGS. 3 and 6 will usually be as shown with respect to the working and reference electrode portions, even the position of the counter electrode within the electrochemical measurement portion is not critical.

The solvent for the test solution will normally be an aqueous medium, which may be up to about 40 weight percent of other polar solvents, particularly solvents having from 1 to 6, more usually of from 1 to 4, carbon atoms, including alcohols, dimethylformamide and dimethylsulfoxide, dioxane and the like. Usually, the cosolvents will be present in less than about 20 weight percent. Under some circumstances, depending on the nature of the sample, some or all of the aqueous medium could be provided by the sample itself.

The pH for the medium will usually be in the range of 4–10, usually 5–9, and preferably in the range of about 6–8. The pH is chosen to maintain a significant level of binding affinity of the binding members and optimal generation of signal by the signal producing system. Various buffers may be used to achieve the desired pH and maintain the pH during the assay. Illustrative buffers include borate, phosphate, carbonate, tris, barbital and the like. The particular buffer employed is not critical, but in individual assays, one buffer may be preferred over another.

Moderate, and desirably substantially constant, temperatures are normally employed for carrying out the assay. The temperatures for the assay and production of a detectable signal will generally be in the range of about 40–40° C., more usually will be in the range of about 10–35° C., and frequently, will be ambient temperatures, that is, about 15–25° C.

The concentration, in the liquid sample, of analyte which may be assayed will generally vary about $10^{-3}$ to about $10^{-15}$M, more usually from about $10^{-5}$ to $10^{-10}$M. Considerations such as the concentration of the analyte of a interest and the protocol will normally determine the concentration of the other reagents.

With the test device and method of the invention, one may also assay a test solution for a plurality of analytes such as toxic chemicals, or screen for one or more of a plurality of analytes. In one embodiment, the test device includes multiple measurement portions, each of which has a distinctive receptor specific for one of several haptens, which are chosen, in part, so as not to interfere with any of the analytes of interest. The test solution (and control solution), where appropriate is formed by mixing together in an aqueous medium the sample and a plurality of liposome conjugates each of which comprises (a) one of the analytes and (b) a hapten which will bind specifically to one of the receptors in one of the measurement portions of the device. Thus, the strip contains a separate measurement portion for each analyte. A mixture of specific binding materials for each of the analytes is non-diffusively bound to the absorbent material in a single competitive binding portion between the contact portion and the measurement portions. The conjugate of each of the analytes to be determined in this embodiment of the invention, may include a marker which is detectable distinctly from the other markers. With different encapsulated dyes, the results of the assay can be "color coded". Alternatively, each analyte may be determined by assignment of each conjugate/analyte to its own measurement portion for concentration and measurement.

In an alternative multiple-analyte embodiment, the measurement portion has bound thereto separate receptors capable of binding different analyte-liposome conjugates through the recognition of the receptors for separate haptens on the different analyte-liposome conjugates. Using such a device, it is possible to conduct a screening assay to determine, for example, whether any of a group of analytes is present in the sample. Alternatively, the liposomes attached to each analyte can have a different dye encapsulated, and a multi-wavelength detector can be used in a measurement portion, such as an egg-white avidin portion.

As a matter of convenience, the present device can be provided in a kit in packaged combination with predetermined amounts of reagents for use in assaying for an analyte or a plurality of analytes. Aside from the absorbent test device and the analyte-liposome conjugate, other additives such as ancillary reagents may be included, for example, stabilizers, buffers, and the like. The relative amounts of the various reagents may be varied widely, to provide for concentration in solution of the reagents which substantially optimizes the sensitivity of the assay. The reagents can be provided as dry powders, usually lyophilized, including excipients, which on dissolution will provide for a reagent solution having the appropriate concentrations for performing the assay. The kit or package may include other components such as standards of the analyte or analytes (analyte samples having known concentrations of the analyte).

Figure 4:
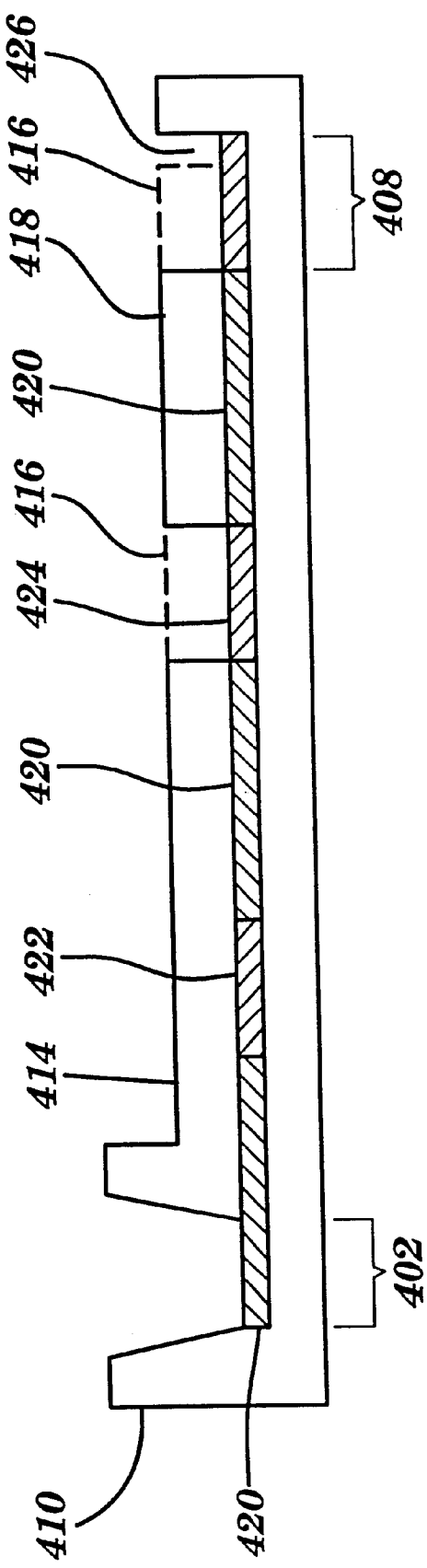
FIG. 4 is a schematic of a cross-section of a commercially useful test device in accordance with the invention.

FIG. 4 is a schematic of a cross-section of a commercially useful test device in accordance with the invention. Absorbent material 420 is supported on strip holder 410, which may be composed of any inert rigid or semi-rigid support material and is preferably composed of plastic. As described above in connection with FIGS. 1 and 2, absorbent material 420 includes contact portion 402, competitive binding portion 422 having a binding material for the analyte of interest non-diffusively bound thereto, and measurement portion 424, having a receptor for a conjugate of the analyte and marker-encapsulating liposomes non-diffusively bound thereto. In the embodiment of the invention shown in FIG. 4, the absorbent material of the test device also includes end-point indicator portion 408, as described below. Compartment covers 414 and 418 provide further support and protection for absorbent material 420. Covers 414 and 418, which are constructed of the same or similar rigid or semi-rigid support materials as strip holder 410, may, with strip holder 410, comprise a single molded piece. Alternatively, covers 414 and 418 may be prepared from a transparent material which allows viewing of absorbent material 420, and may be connected to strip holder 410.

The device shown in FIG. 4 further include windows 416 which provide visual access to measurement portion 424 and end-point indicator portion 408 of the absorbent material. Windows 416 may be made from a transparent material such as plastic or glass. Alternatively, they may be prepared from an opaque material such as a colored plastic incorporating holes through which absorbent material 420 may be seen. Air vent 426 provides an outlet for air forced out of absorbent material 420 as a test solution or control solution migrates along absorbent material 420 from contact portion 402 to end-point indicator portion 408.

The embodiment shown in FIG. 4 provides a sturdy, portable, contamination-resistant test device suitable for use in the field. In use, a test solution containing the appropriate analyte-liposome conjugate, and known or suspected to contain the analyte, is spotted or dropped onto contact portion 402 of absorbent material 420. Contact portion 402 is wet with the test or control solution, or a carrier solution or wicking reagent after initial application of the test or control solution, until the solution traverses the absorbent material 420 from contact portion 402 to end-point indicator portion 408. Competitive binding between the analyte and the conjugate occurs in competitive binding portion 402. Conjugate which is not bound in competitive binding portion 422 is accumulated in measurement portion 424 as a result of the binding reaction between the conjugate and the receptor non-diffusively bound to measurement portion 424.

The signal from the marker may be visually read through window 416 over measurement portion 424. Alternatively, the signal from accumulated liposome-encapsulated marker may be instrumentally read by, for example, a spectrophotometer which is adapted for use with the device in accordance with the invention.

The present invention is applicable to procedures and products for determining a wide variety of analytes. As representative examples of types of analytes, there may be mentioned: environmental and food contaminants, including pesticides and toxic industrial chemicals; drugs, including therapeutic drugs and drugs of abuse; hormones, vitamins, proteins, including antibodies of all classes; peptides; steroids; bacteria; fungi; viruses; parasites; components or products of bacteria, fungi, viruses, or parasites; allergens of all types; products or components of normal or malignant cells; etc. As particular examples, there may be mentioned $T_4$; $T_3$; digoxin; hCG; insulin; theophylline; leutinizing hormones and organisms causing or associated with various disease states, such as streptococcus pyogenes (group A), Herpes Simplex I and II, cytomegalovirus, chlamydiae, etc.

As hereinabove indicated, the assay may be qualitative (presence or absence of certain level of analyte) or quantitative or semi-quantitative. The preparation of suitable standards and/or standard curves (the term "standard curve" is used in a generic sense to include a color chart) is deemed to be within the scope of those skilled in the art from the teachings herein.

The method of the invention, and preparation and use of the test device in accordance with the invention, are illustrated by the following Examples.

EXAMPLES

Materials

Alachlor was purchased from Chem Service (West Chester, Pa.). Bovine serum albumin (BSA), N-succinimidyl-S-acetylthioacetate (SATA), dipalmitoyl phosphatidyl ethanolamine (DPPE), cholesterol, poly (vinylpyrrolidone) (PVP, 10,000 mol. wt.), Tween-20, triethylamine, Molybdenum Blue spray reagent, Isosulfan Blue and Sephadex G-50 were purchased from Sigma (St. Louis, Mo.). Dipalmitoyl phosphatidyl choline (DPPC) and dipalmitoyl phosphatidyl glycerol (DDPG) were obtained from Avanti Polar Lipids (Alabaster, Ala.). Sulforhodamine B was purchased from Eastman (Rochester, N.Y.), and Fast Green FCF from Allied Chemical (New York, N.Y.). Carnation non-fat dry milk powder (CNDM) was obtained locally. Protein assay dye reagent, goat anti-rabbit IgG alkaline phosphatase conjugate and the substrates for alkaline phosphatase were purchased from Bio-Rad (Hercules, Calif.). Egg white avidin was obtained from Molecular Probes (Eugene, Oreg.). Whatman (Maidstone, UK) silica gel TLC flexible plates and preparatory silica get plates, both containing fluorescent indicator, were used. Plastic-backed nitrocellulose membranes with pore size >3 $\mu$m were obtained from Schleicher and Schull (Keene, N.H.). A Paasch VL airbrush (Texas Art Supply, Houston, Tex.) was used for applying the antibody and egg white avidin to the membrane. The rabbit anti-Alachlor IgG used in preliminary investigations was supplied by ImmunoSystems (Scarborough, Me.). Subsequent supplies of antiserum were provided by the Cornell University College of veterinary Medicine.

EXAMPLE 1

Preparation of Materials and Reagents

Conjugate and Antibody Production

Alachlor was conjugated to BSA by modification of a published method, as described in Reeves, et al. *Anal. Lett.*, 26 (1993) 1461, hereby incorporated by reference. Antibodies to the immunogenic conjugate were raised in New Zealand white rabbits by standard procedures. The antibodies produced were purified by the caprylic acid-ammonium sulfate precipitation method, described in McKinney, et al., *J. Immunol. Methods*, 96 (1987) 271, hereby incorporated by reference.

Antibody and Avidin Immobilization

In the strip assay, a protein-binding membrane (absorbent material) with a plastic backing to provide rigidity was required, and nitrocellulose membrane supported in this manner was found to be the most suitable. An airbrush was used to dispense the antibody and egg white avidin solutions for immobilization. The membrane was cut to a desired size (7.9 cm high and a suitable width for later subdivision into strips 5 mm wide), thoroughly wetted with 10% methanolic TBS (tris buffered saline, pH 7.0) and dried before application of antibody and avidin solutions. The membrane sheet was mounted on a mobile platform that moved at a constant rate in front of the airbrush used to spray the antibody solution at a concentration between 0.2 and 1 mg ml$^{-1}$ (depending on preparation) onto the competitive binding portion of the membrane, and egg white avidin solution at 1 mg ml$^{-1}$ onto the measurement portion of the membrane. The protein bands were allowed to vacuum dry for 1 hour.

After applying antibody and egg white avidin to the nitrocellulose sheets, it was necessary to block the membrane to reduce non-specific binding and to aid the mobility of the liposomes. Both PVP and BSA were found to be suitable for this purpose, but the former was less expensive and more tractable and was routinely used as the blocking agent. Non-uniform migration of liposomes with certain batches of membrane, can be alleviated by the use of very low levels of detergent in the blocking solution. Tween-20 at 0.002% was found suitable for this purpose, and at this level of application it did not cause lysis of the liposomes during the 8-min analysis run.

The coated nitrocellulose sheet was then immersed in blocking agent (a solution of 2% polyvinylpyrrolidone and 0.002% Tween-20 in TBS) for 1 hour on a rotating shake and dried under vacuum for 3–4 hours. Prepared sheets were stored at 4° C. in the presence of silica gel desiccant until ready for use. The sheets were cut into strips using a paper cutter when required. The final strips were 5×79 mm with a 5 mm long antibody zone 15 mm above the bottom of the strip and a similar egg white avidin zone 35 mm from the bottom.

Analyte-lipid Conjugation

To provide the requisite antigenic sites (epitopes) on the surface of the liposomes for the competitive assay format, it is necessary to form a conjugate between the analyte molecule and a lipid, DPPE, which is then incorporated into the liposome bilayer.

For conjugation of the Alachlor to DPPE, a thiolating reagent, SATA, described in Duncan, et al., *Anal. Biochem.*, 132 (1983) 68, which is hereby incorporated by reference, was used as the coupling agent based on a modification of a procedure reported in Feng, et al., *J. Agric. Food Chem.* 38 (1990) 59, hereby incorporated by reference. Twenty mg of DPPE were suspended in 3 ml of 0.7% triethylamine in chloroform and sonicated under nitrogen for 1 minute in a 450° C. bath. To the DPPE, 2 molar equivalents of SATA in 1 ml of the same solvent were added slowly. The reaction flask was capped and stirred at room temperature for ca. 20 minutes, the end point of the reaction being indicated by the clearing of the mixture. The solvent was removed on a rotary vacuum evaporator, and 2 ml of 30 mM hydroxylamine hydrochloride in methanol, adjusted to pH 8.2 with NaOH, were added. The reaction mixture was vortexed vigorously and stirred at 45° C. for 1 hour under nitrogen, maintaining the pH at 8.2 using dilute NaOH in methanol. A 2.8 molar excess (to DPPE) of Alachlor in 1 ml of 30 mM hydroxylamine, pH 8.2 in methanol, was added to the reaction flask. The reaction mixture was stirred at 45° C. for 2 hours, with the pH being maintained at 8.2, and the reaction was allowed to continue at 45° C. overnight (ca. 17 hours). The product was purified on a preparatory silica gel plate using the solvent system chloroform-acetone-methanol-glacial acetic acid-water (60:20:20:5:4, v/v). The purified Alachlor-DPPE conjugate was quantified by Bartlett's phosphorous assay described in Bartlett, *J. Biol. Chem.*, 234 (1959) 466, which is hereby incorporated by reference.

Because radioactive Alachlor was not available for use as a tracer, confirmation of the successful conjugation reaction was achieved by a combined thin-layer chromatographic and an enzyme immunostaining method described in Mattsby-Baltzer, *Eur. J. Biochem.*, 138 (1984) 333, hereby incorporated by reference, using an anti-Alachlor antibody supplied by ImmunoSystems. The procedure involved the duplicate chromatographic analysis of the reaction mixture on TLC plates. Whatman Silica Gel/UV plates were prewashed in the solvent described above and dried, and the samples were run in the same solvent. One of the TLC plates was dried, blocked for 1 hour in a solution of 1% BSA and 0.5% CNDM in TBS, washed three times for 10 minutes each in TBST (TBS containing 0.05% Tween-20), and placed overnight in a solution containing the antibody to Alachlor (20 $\mu$g/ml in TBST). The plate was washed three times for 10 min each in TBST and placed in a solution containing a goat anti-rabbit alkaline phosphatase conjugate (stock diluted 1:3000 with TBST containing 0.02% BSA) for 2 hours. The plate was washed as before and developed with the substrate for alkaline phosphatase (nitroblue tetrazolium in aqueous DMF with magnesium chloride and 5-bromo-4-chloro-3-indolyl phosphate in DMF, prepared according to the manufacturer's instructions). When color development was complete (10 min), the plate was washed in distilled water and dried. A purple spot indicated the presence of Alachlor. The other TLC plate was sprayed with molybdenum blue reagent (1.3% molybdenum oxide in 4.2 M sulfuric acid) which is specific for phospholipids. The Alachlor-DPPE spot appeared purple with the alkaline phosphatase substrate stain and blue with the molybdenum blue spray reagent.

Preparation of Dye-encapsulated Alachlor-tagqed Liposomes

Liposomes were formed by the reversed-phase evaporation method, as described in Szoka, et al., *Biochim. Biophys. Acta*, 601 (1980) 559, and O'Connell, et al., *Anal. Chem.*, 31 (1985) 142, the disclosures of which are hereby incorporated by reference, from a mixture of DPPC, cholesterol, DPPG, and Alachlor-DPPE conjugate in a molar ration of 5:5:0.5:0.01. Forty-three $\mu$mol of this mixture were dissolved in 4.2 ml of a solvent mixture containing chloroform-isopropyl ether-methanol (6:6:1, v/v). This solution was warmed to 45° C. and 0.7 ml of the dye solution was added with swirling. This mixture was sonicated for 5 minutes under a low flow of nitrogen. The organic phase was removed under vacuum on a rotary evaporator at 40° until all frothing had stopped. An additional 1.3 ml aliquot of the dye solution was added, and the liposomes were then sequentially extruded twice through each of two polycarbonate filters of decreasing pore sizes of 1.0 $\mu$m and 0.4 $\mu$m. The diameters of the liposome preparations were measured by laser scattering in a LA-900 particle size distribution analyzer (Horiba, Irvine, Calif.), using the manufacturers method, except that the usual sonication step was omitted to avoid lysis (rupture) of the liposomes. Finally, to remove any unencapsulated dye, the liposomes were gel filtered on a 1×14 cm Sephadex G-50 column and dialyzed overnight against TBS at 4° C. When stored at 4° C., there was no significant leakage of dye over a period of 9 months as described below.

Sulforhodamine B was chosen as the dye for encapsulation, as described in O'Connell, above, and Chen, et al., *Anal. Biochem.*, 172 (1988) 61, hereby incorporated by reference, because of its fluorescence and high visible extinction coefficient. To prepare the dye, 20 mM Tris was used to buffer the dye solution. The pH was adjusted to 7.0 with NaOH to effect dissolution. The final solution contained 100 mM dye in 20 mM Tris at a pH of 7.0 with an osmolarity approximately equal to TBS, which was the buffer routinely used in all aqueous operations of the experiments. In some experiments 200 mM Sulforhodamine B was used to give a greater color intensity on the strips.

Because Sulforhodamine B is highly fluorescent and this fluorescence undergoes self-quenching when encapsulated, the integrity of the liposomes can be determined by measuring fluorescence intensity before and after lysis. Total and almost instantaneous lysis of the liposomes was effected by addition of a solution (final concentration =30 mM) of n-octyl-β-D-glucopyranoside at room temperature. For these fluorescence experiments, the dye was excited at a wavelength of 543 nm and fluorescence measured at the emission wavelength of 596 nm.

In some experiments the non-fluorescent dyes Isosulfan Blue and Fast Green FCF were encapsulated by the same methods as Sulforhodamine B.

Characteristics of Liposomes

Liposomes were prepared by the reversed-phase evaporation method described in Szoka and O'Connell, above, but without extrusion through polycarbonate filters, giving a high yield of liposomes. However, these heterogeneously sized liposomes did not migrate evenly on the test strips used in the assay. This was improved by passing the preparations sequentially twice through each of two polycarbonate filters of 1.0 and 0.4 μm nominal pore diameter. Liposomes passed only through the 1.0 μm filter had a mean diameter of 1.82 μm, with a standard deviation of 0.8, while those passed through both filters had a mean diameter of 0.68 μm with a standard deviation of 0.12. This discrepancy between the size of the pores on the polycarbonate filters and the final size of the liposomes is not surprising, as the liposomes are very flexible, and can thus "squeeze" through a pore of smaller diameter. The liposomes of 0.68 μm diameter were a much more homogeneous population than those of 1.82 μm diameter, and both populations migrated more evenly on the nitrocellulose sheets than did the unextruded liposomes. Passing the preparation through an even smaller sized filter (0.2 μm) did not improve the migration behavior, and reduced the yield considerably. Consequently, liposomes that had been passed through the 1.0 and 0.4 μm filters were used in all subsequent experiments.

The absorption spectrum of dilute, free Sulforhodamine B gave a peak at 566 nm, with a shoulder at 532 nm. The intact liposomes, containing dye at a concentration sufficiently high to form dimers, as described in Chen, et al., *Anal. Biochem.*, 172 (1988) 61, hereby incorporated by reference, gave a spectrum with peaks at 532 and 568 nm, with the 568 nm peak at 70% of the height of the 532 nm peak. The addition of surfactant to the liposomes caused lysis of the liposomes and consequent dilution of the dye, and thus converted the spectrum to that of the free dye.

The presence of Alachlor on the surface of the liposomes was demonstrated by the reversal, by free Alachlor, of antibody-induced aggregation of the liposomes. The aggregated liposomes could be precipitated by centrifugation.

The liposomes were stored at 4° C., and the temporal stability was studied over time by measuring the percentage of free dye in the preparation, thereby allowing calculation of the percentage of the liposomes that had lysed.

The characteristics of the liposomes used in these studies are shown in Table 1. From the size measurement results, it is possible to calculate that the average volume of a single liposome is $1.7 \times 10^{-10}$ μl. By assuming the dye encapsulated was equal in concentration to the original dye solution used, and by comparing the fluorescence of lysed liposomes to that of standard Sulforhodamine B solutions, it is possible to calculate that there were ca. $1.2 \times 10^8$ liposomes μl$^{-1}$ and that each liposome contained ca. $9.6 \times 10^6$ molecules of dye. Assuming that the average surface area of the DPPC molecules is 71 Å$^2$, and that of cholesterol molecules in a mixed bilayer is 19 Å$^2$, as described in Isaraelachvili, eta al., *Biochim. Biophys. Aeta*, 389 (1975) 13, and given that the DPPE-Alachlor is 0.1 mole % of the total lip, there are ca. 3500 molecules of Alachlor on the outer surface of a single liposome.

TABLE 1

Liposome Characteristics

| | |
|---|---|
| Mean diameter (±S.D.) | 0.68 ± 0.12 μm |
| Volume | $1.7 \times 10^{-10}$ μl |
| Liposome conc. | $1.2 \times 10^8$ lipo μl$^{-1}$ |
| SRB$^a$ conc. | 100 mM |
| SRB$^a$ (molecular)$^b$ | $9.6 \times 10^6$ molec. lipo$^{-1}$ |
| Alachlor conc.$^c$ | $3.5 \times 10^3$ molec. lipo$^{-1}$ |
| Stability | >9 months |

$^a$Sulforhodamine B.
$^b$The number of molecules of SRB per liposome.
$^c$The number of molecules of Alachlor on the outer surface of a single liposome containing 0.1 mole % DPPE-Alachlor.

EXAMPLE 2

Assay format

The assay device configuration consists of a wicking reagent containing Alachlor-tagged liposomes and a test strip comprised of a wick, an immobilized anti-Alachlor zone and an egg white avidin capture zone in sequence. The assay is performed by dispensing 100 μl (2 drops) of the sample or control solution and 50 μl (1 drop) of a three times concentrated TBS buffer into a 10× 75 mm glass test tube, mixing the contents, and adding 50 μl (1 drop) of a liposome solution (stock liposome solution diluted 1:50, dilution varying according to preparation). The test tube is shaken mildly to mix the contents and the test strip is inserted into the tube; the strip is left in the tube until the solution front reaches the end of the strip (about 8 min); the strip is removed and air dried. The color intensity of the antibody zone and the egg white avidin zone are estimated either visually or by scanning densitometry, as described in Reeves, (1993).

The measurement of the extent of the competitive binding reactions of the analyte molecules and the tagged liposomes to the immobilized antibodies was optical. Visual estimation of the color intensity can be used, but for more accurate quantitation during development it was found to be preferable to use a computer scanner and Scan Analysis densitometry software (Biosoft, Ferguson, Mo.) to convert the red coloration into greyscale readings that can be measured.

A series of analyte determinations were made as described above with a series of Alachlor standards of varying concentrations. A decrease in color of the antibody zone with increasing concentrations of added Alachlor, and a concomitant increase in the color of the egg white avidin zone, was observed.

Figure 5:
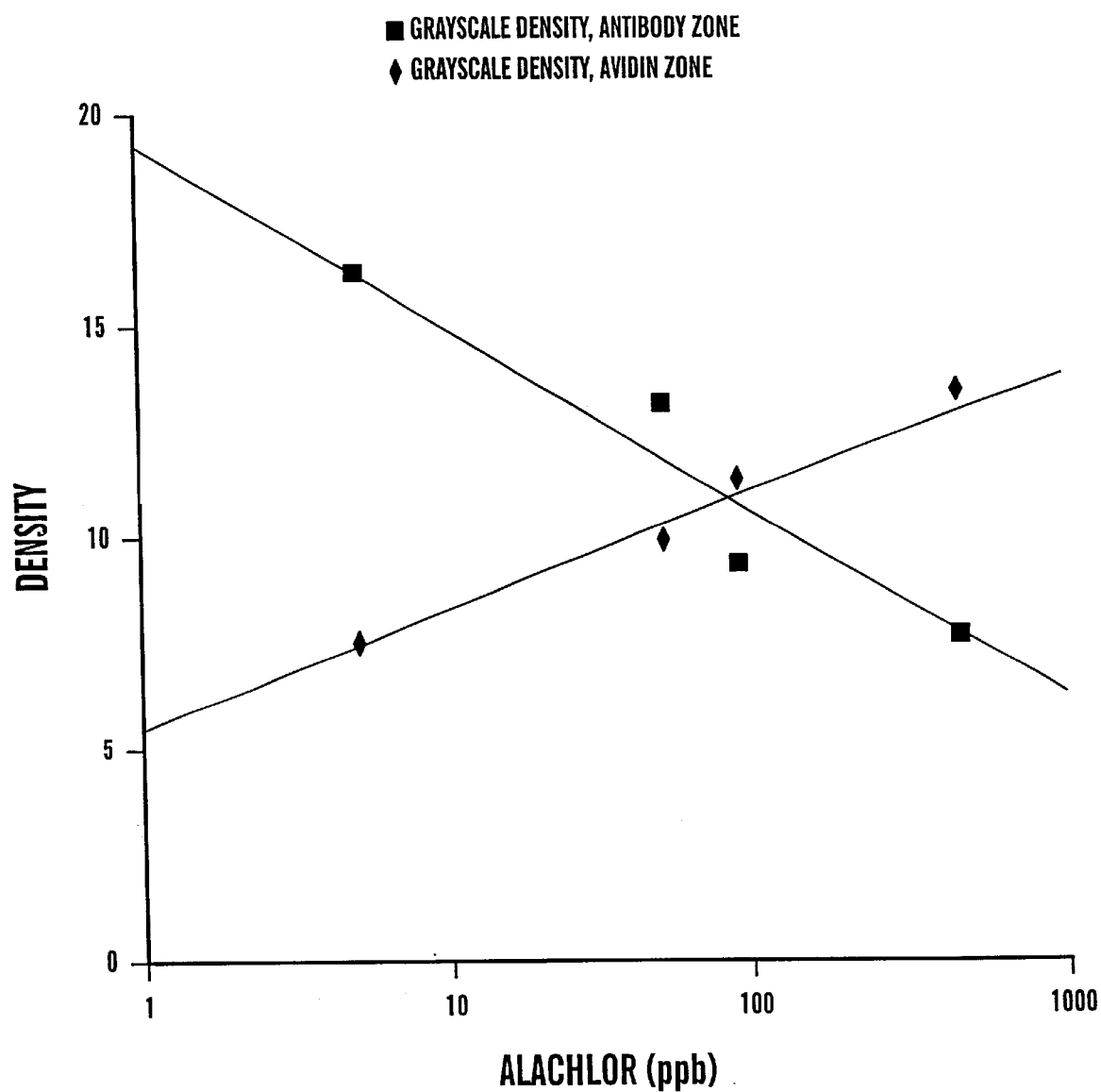
FIG. 5 is a plot of dose-response data obtained for samples containing various concentrations of Alachlor, as described in greater detail in Example 2, below.

Dose-response data obtained by scanning densitometry of strips run in the presence of various concentrations of Alachlor are shown in FIG. 5, which is a graph of greyscale density versus Alachlor concentration (ppb), measured in both the antibody and avidin zones. The response in both the antibody and avidin zones varied logarithmically when measured using scanning densitometry, and both were estimated to be able to detect 5–10 μg/l Alachlor. When these strips were assessed visually, a similar determination could be made, but at low levels of added Alachlor it was somewhat easier to detect increases of red color over a white control (avidin zone) than decreases in color intensity (antibody zone).

These examples are included to illustrate the practice of the invention. However, numerous variations and alternatives for the structure, components and use of the test device of the invention are possible. For example, a test device packaged as part of a commercial kit might include special holders for individual strips, in which openings are provided for sample application and optical readout, for example, as shown in FIG. 4. In such a configuration, the strips could be run in any orientation, e.g., lateral, instead of vertical flow.

In an alternative embodiment of the invention, a dual-strip test device as shown in FIG. 2 may be employed. In this design, after application of the protein zones, the strip is divided in two by removal of a very thin strip of nitrocellulose from the plastic backing, thereby providing two identical strips with a hydrophobic separation to prevent solution cross-talk. A tolerance level control is applied to the strip adjacent to the sample, and both are run simultaneously. This verifies the strip performance and provides a more quantitative interpretation of the strip results. As described above, multi-analyte assays may also be conducted using the test device and method of the invention.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A test device for detecting or determining an analyte in a test solution, said test device comprising:

an absorbent material, comprising:
  a contact portion proximate to a first end of said absorbent material for contact with and uptake of said test solution;
  an electrochemical measurement portion at a location on said absorbent material which is positioned away from the first end; and
  a competitive binding portion positioned between and segregated from said contact portion and said measurement portion on said absorbent material and having a binding material for the analyte non-diffusively bound to said competitive binding portion;
  said electrochemical measurement portion comprising a working electrode portion and a counter electrode portion, and further comprising a reference electrode portion positioned between and segregated from said working electrode portion and said counter electrode portion on said absorbent material, wherein said working electrode portion is positioned between said competitive binding portion and said reference electrode portion on said absorbent material, said working, reference, and counter electrode portions are electrically connected with one another, and wherein either said absorbent material further comprises a liposome lysing portion positioned between said competitive binding portion and said working electrode portion, wherein said liposome lysing portion is segregated from said competitive binding portion and has a liposome lysing agent non-diffusively bound thereto, or said working electrode portion has a liposome lysing agent non-diffusively bound thereto.

2. A test device according to claim 1, said working electrode portion further having a marker accumulating agent non-diffusively bound thereto.

3. A test device for detecting or determining an analyte in a test solution, said test device comprising:

an absorbent material, comprising:
  a contact portion proximate to a first end of said absorbent material for contact with and uptake of said test solution;
  an electrochemical measurement portion at a location on said absorbent material which is positioned away from the first end; and
  a competitive binding portion positioned between and segregated from said contact portion and said measurement portion on said absorbent material and having a binding material for the analyte non-diffusively bound to said competitive binding portion;
  said electrochemical measurement portion comprising an indicator electrode portion and a reference electrode portion, wherein said indicator electrode portion and said reference electrode portion are electrically connected with one another, and said indicator electrode portion is positioned between and segregated from said competitive binding portion and said reference electrode portion on said absorbent material, and wherein either said absorbent material further comprises a liposome lysing portion positioned between said competitive binding portion and said indicator electrode portion, wherein said liposome lysing portion is segregated from said competitive binding portion and has a liposome lysing agent non-diffusively bound thereto, or said indicator electrode portion has a liposome lysing agent non-diffusively bound thereto.

4. A test device for detecting or determining an analyte in a test solution, said test device comprising:

an absorbent material, comprising:
  a contact portion proximate to a first end of said absorbent material for contact with and uptake of said test solution;
  an electrochemical measurement portion at a location on said absorbent material which is positioned away from the first end; and
  a competitive binding portion positioned between and segregated from said contact portion and said measurement portion on said absorbent material and having a binding material for the analyte non-diffusively bound to said competitive binding portion;
  said electrochemical measurement portion comprising a working electrode portion, a reference electrode portion, and a counter electrode portion, wherein each of said electrode portions is segregated from one another on said absorbent material, said working, reference, and counter electrode portions are electrically connected with one another, and wherein either said absorbent material further comprises a liposome lysing portion positioned between said competitive binding portion and said working electrode portion, wherein said liposome lysing portion is segregated from said competitive binding portion and has a liposome lysing agent non-diffusively bound thereto, or said working electrode portion has a liposome lysing agent non-diffusively bound thereto.

5. A test device according to claim 4, said working electrode portion further having a marker accumulating agent non-diffusively bound thereto.

6. A test device for detecting or determining an analyte in a test solution, said test device comprising:

an absorbent material, comprising:
- a contact portion proximate to a first end of said absorbent material for contact with and uptake of said test solution;
- an electrochemical measurement portion at a location on said absorbent material which is positioned away from the first end; and
- a competitive binding portion positioned between and segregated from said contact portion and said measurement portion on said absorbent material and having a binding material for the analyte non-diffusively bound to said competitive binding portion;
- said electrochemical measurement portion comprising an indicator electrode portion and a reference electrode portion, wherein said indicator electrode portion and said reference electrode portion are segregated from one another on said absorbent material and are electrically connected with one another, and wherein either said absorbent material further comprises a liposome lysing portion positioned between said competitive binding portion and said indicator electrode portion, wherein said liposome lysing portion is segregated from said competitive binding portion and has a liposome lysing agent non-diffusively bound thereto, or said indicator electrode portion has a liposome lysing agent non-diffusively bound thereto.

* * * * *